United States Patent
Strobl

(10) Patent No.: US 9,265,885 B2
(45) Date of Patent: Feb. 23, 2016

(54) SYSTEMS AND METHOD FOR ASSESSING FUNCTIONALITY OF DUAL CHECK VALVE ARRANGEMENTS IN MEDICAL TUBING SETS

(75) Inventor: Geoffrey S. Strobl, Williamsburg, OH (US)

(73) Assignee: LIEBEL-FLARSHEIM COMPANY LLC, Hazelwood, MO (US)

( * ) Notice: Subject to any disclaimer, the term of this patent is extended or adjusted under 35 U.S.C. 154(b) by 1190 days.

(21) Appl. No.: 13/201,632

(22) PCT Filed: Sep. 28, 2010

(86) PCT No.: PCT/US2010/050491
§ 371 (c)(1),
(2), (4) Date: Aug. 16, 2011

(87) PCT Pub. No.: WO2011/041290
PCT Pub. Date: Apr. 7, 2011

(65) Prior Publication Data
US 2012/0046546 A1    Feb. 23, 2012

Related U.S. Application Data

(60) Provisional application No. 61/246,714, filed on Sep. 29, 2009.

(51) Int. Cl.
*A61M 5/50* (2006.01)
*A61M 5/168* (2006.01)
(Continued)

(52) U.S. Cl.
CPC ......... *A61M 5/16854* (2013.01); *A61M 5/5086* (2013.01); *A61B 6/548* (2013.01); *A61M 5/007* (2013.01); *A61M 5/14546* (2013.01); *A61M 2205/273* (2013.01); *A61M 2205/3331* (2013.01)

(58) Field of Classification Search
CPC ............... A61M 5/16854; A61M 5/14546; A61M 5/5086; A61M 5/16831; A61M 5/007; A61M 2205/273; A61M 5/3331; A61M 6/548
USPC ............................................. 604/67
See application file for complete search history.

(56) References Cited

U.S. PATENT DOCUMENTS 4,284,097 A    8/1981    Becker et al.
5,205,819 A    4/1993    Ross et al.
(Continued)

FOREIGN PATENT DOCUMENTS

JP    2008-058284 A    3/2008
WO    2006/060688 A2    6/2006

*Primary Examiner* — Bhisma Mehta
*Assistant Examiner* — Jenna Zhang
(74) *Attorney, Agent, or Firm* — Marsh Fischmann & Breyfogle LLP

(57) ABSTRACT

A dual one-way check valve arrangement (300) that may be used for assessing an operating condition of at least one of first and second check valves (304, 308) situated in series along/within a section of a patient-specific section of tubing (244). A pressure sensor (332) may be associated with at least part of the flow path between the first and second check valves (304, 308) and may be operable to provide an indication of a failed condition of at least one of the first and second check valves (304, 308). In one embodiment, the pressure sensor (332) may change from a first state to a second state upon fluid pressure within the flow path between the first and second check valves (304, 308) falling below a predetermined level. For instance, the predetermined level may be a cracking pressure of at least one of the first and second check valves (304, 308). The change in state may be visually discernible on an exterior of the pressure sensor (332).

25 Claims, 12 Drawing Sheets

(51) Int. Cl.
  *A61M 5/00* (2006.01)
  *A61M 5/145* (2006.01)
  *A61B 6/00* (2006.01)

(56) References Cited

U.S. PATENT DOCUMENTS

| | | | |
|---|---|---|---|
| 5,354,273 A * | 10/1994 | Hagen | A61M 5/14526 128/DIG. 12 |
| 5,688,244 A * | 11/1997 | Lang | A61M 5/16854 200/83 W |
| 5,713,240 A | 2/1998 | Engelmann | |
| 2004/0167495 A1 | 8/2004 | Neftel | |
| 2005/0034524 A1 | 2/2005 | Saida et al. | |
| 2005/0104444 A1 * | 5/2005 | Callan | A61M 5/007 303/114.1 |
| 2005/0234428 A1 * | 10/2005 | Spohn | A61M 5/007 604/533 |
| 2008/0171981 A1 * | 7/2008 | Khan | A61M 5/346 604/111 |
| 2010/0286544 A1 * | 11/2010 | Tanaka | A61M 1/04 600/532 |
| 2012/0053457 A1 * | 3/2012 | Fago | A61M 5/14546 600/432 |

* cited by examiner

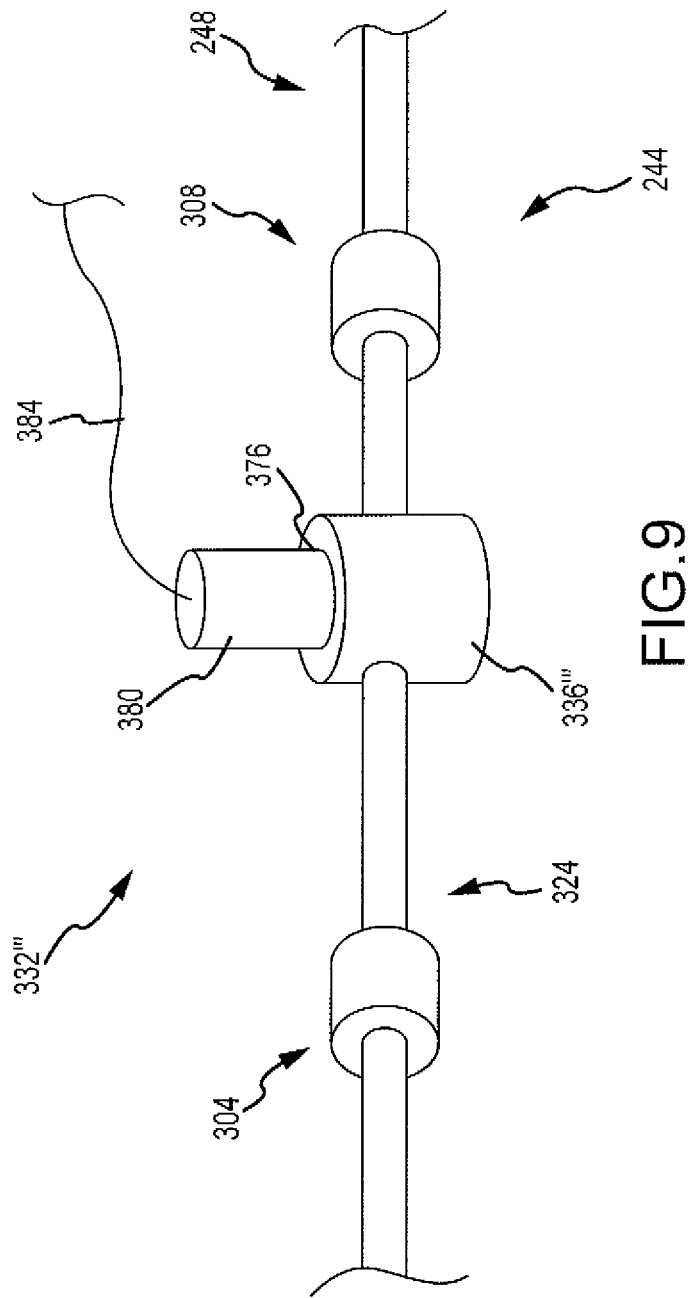

SYSTEMS AND METHOD FOR ASSESSING FUNCTIONALITY OF DUAL CHECK VALVE ARRANGEMENTS IN MEDICAL TUBING SETS

CROSS-REFERENCE TO RELATED APPLICATIONS

This patent application claims priority to U.S. Provisional Patent Application Ser. No. 61/246,714 entitled "SYSTEMS AND METHOD FOR ASSESSING FUNCTIONALITY OF DUAL CHECK VALVE ARRANGEMENTS IN MEDICAL TUBING SETS" filed on 29 Sep. 2009.

FIELD OF THE INVENTION

The present invention generally relates to the field of medical fluid delivery systems and, more particularly, to systems and methods for monitoring an operating condition of one or more check valves of a medical fluid delivery system.

BACKGROUND

Various medical procedures require that one or more medical fluids be injected into a patient. For example, medical imaging procedures oftentimes involve the injection of contrast media into a patient, possibly along with saline and/or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is designed to interface with (e.g., contact and/or temporarily interconnect with) an appropriate syringe plunger driver that is incorporated into the powerhead, such that operation of the syringe plunger driver axially advances the associated syringe plunger inside and relative to a barrel of the syringe. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

One way to categorize syringes used by power injectors is the manner in which they are filled or loaded with fluid. Power injector syringes may be pre-filled—syringes that are filled with fluid at one facility and then shipped to another facility (e.g., an end-use facility). Empty syringes may be shipped to the end-use facility, and may then be filled with fluid in at least two general manners. An empty syringe may be filled with fluid at one location within the end-use facility (e.g., at a filling station), and then transferred to another location within the end-use facility (e.g., an imaging suite) where the fluid-containing syringe is then installed on a power injector. Alternatively, an empty syringe may be installed on a power injector at the end-use facility (e.g., in an imaging suite) and then loaded or filled with fluid.

Individual empty syringes may be filled in accordance with the foregoing from what may be characterized as a single dose container. In this case, the syringe is used for a single injection on a single patient. Any contrast media remaining in the syringe after this single injection is thereby wasted. The entire tubing set extending from the power injector to the patient (including the various components that may be incorporated into the tubing set, such as one or more valves and a catheter) is also discarded.

SUMMARY

A first aspect of the present invention is directed to a medical fluid tubing set that includes a first section of medical fluid tubing, first and second check valves, and a pressure sensor. The first and second check valves are situated in series along/within the first section of medical fluid tubing, and the pressure sensor is associated with a space within the first section of medical fluid tubing that is located at least somewhere between the first and second check valves.

A number of feature refinements and additional features are applicable to the first aspect of the present invention. These feature refinements and additional features may be used individually or in any combination. As such, each of the following features that will be discussed may be, but are not required to be, used with any other feature or combination of features of the first aspect. The following discussion is applicable to the first aspect, up to the start of the discussion of a second aspect of the present invention.

In an embodiment, the pressure sensor may provide the function of monitoring for a failed condition of the medical fluid tubing set. For instance, the failed condition may be when at least one of the first and second check valves is at least presumed to have failed (e.g., has allowed fluid to flow in more than one direction through the check valve; when a check valve has allowed for an undesired backflow). In an embodiment, the pressure sensor may be operable to provide an indication that at least one of the first and second check valves is at least presumed to have failed. As an example, the indication may be at least one of visual, audible, tactile, or any combination thereof. The pressure sensor may be useful in determining whether one or more portions of the medical fluid tubing set may need to be replaced before a subsequent injection procedure. In an embodiment, the first section of medical fluid tubing may be patient-specific. Moreover, the medical fluid tubing set may further include a second section of medical tubing fluidly interconnectable to the first section of medical tubing, and the second section of medical tubing may be reusable (e.g., for use with multiple patients, or a multi-patient tubing section). In this regard, the reusable portion of the medical fluid tubing set may be discarded and/or replaced if the pressure sensor determines that a failed condition has occurred or otherwise provides an indication that at least one of the first and second check valves is at least presumed to have failed.

In an embodiment, the pressure sensor may be responsive to a fluid pressure in a first region of the first section of medical fluid tubing. In one variation, this first region may be located between the first and second check valves. For instance, the pressure sensor may respond to the fluid pressure by changing from a first state to a second state upon fluid pressure within the first region falling below a predetermined level. In one arrangement, the predetermined level may be a cracking pressure (e.g., a pressure differential required to open the corresponding check valve) of at least one of the first and second check valves. In another arrangement, the predetermined level may be the cracking pressure of each of the first and second check valves.

The pressure sensor may be subject to a number of characterizations. In an embodiment, the pressure sensor may be situated on the first section of medical fluid tubing. Further, the pressure sensor may be situated in series with the first and second check valves, and/or may be situated between the first and second check valves. The pressure sensor may also be fluidly interconnectable with the first section of medical fluid tubing.

In an embodiment, the pressure sensor may include a movable element. For instance, the movable element of the pressure sensor may be operable to perform at least one of measuring fluid pressure and providing an indication related to the measured fluid pressure. In a variation, a first position of the movable element may be associated with a proper functioning of the first and second check valves and a second position of the movable element may be associated with at least a presumed failure of at least one of the first and second check valves. These two positions of the movable element may be viewable or discernable from an exterior of the pressure sensor (e.g., by providing a change in shape of the exterior of the pressure sensor).

In one arrangement, the pressure sensor may further include a biasing member (e.g., compression spring, wave spring) interconnected with the movable element, and which biases the movable element into one of its two primary positions. Multiple biasing members could be used as well. At least one biasing member may bias the movable element into either the first position (that which is associated with a presumed proper functioning of the first and second check valves) or the second position (that which is associated with at least one of the first and second check valves at least being presumed to have failed). Additionally, the pressure sensor may further include a housing constructed of any appropriate material (e.g., plastic, metal). In one setup, the movable element may include a portion that protrudes from the housing in the first position and is substantially concealed by the housing in the second position. In another setup, the movable element may include a portion that protrudes from the housing in the second position and that is substantially concealed by the housing in the first position.

The above-noted movable element may be characterized as being movable between two different positions—one being associated with the first and second check valves being presumed to be functional, and the other being associated with at least one of the first and second check valves being presumed to have failed. This change in position of the movable element may be visually perceptible on an exterior of the pressure sensor (e.g., by viewing an exterior of the pressure sensor). Movement of the movable element between two different positions may also be characterized as providing a visually perceptible change in shape of the exterior of the pressure sensor.

In another arrangement, at least a portion of the movable element may be discernable in one of the first and second positions and may not be discernable in the other of the first and second positions. For instance, a failed condition of at least one of the first and second check valves may be presumed when the portion of the movable element is not discernable and a properly functioning condition of each of the first and second check valves may be presumed when the portion of the movable element is discernable, or vice versa. In one variation, the housing may include a window (e.g., a semi-transparent or a transparent portion). In one embodiment, the portion of the movable element may be discernable through the window in one of the first and second positions and may not be discernable in the other of the first and second positions. In another embodiment, the movable element may be discernable through the window in each of the first and second positions, and a change in shape of the movable element may be discerned by a movement between the first and second positions. In yet another embodiment, at least part of the movable element may be discernable in one of the first and second positions, and the entirety of the movable element may not be discernable through the window in the other of the first and second positions.

The movable element may be in any appropriate form. For instance, in one variation, the movable element may be in the form of a substantially non-deformable piston—the piston may move other than by a deformation or change in shape between the two noted positions. In another variation, the movable element may include a diaphragm. An exterior of this diaphragm may experience a visually-discernable shape change in response to an at least presumed failed condition of at least one of the first and second check valves.

In an embodiment, the pressure sensor may include a port that is fluidly interconnectable with the first section of medical fluid tubing. The pressure sensor may also include a pressure transducer interconnected to the port. It will be appreciated that the pressure transducer may appropriately measure or monitor the fluid pressure in the first section of medical tubing and may communicate with any appropriate device (e.g., computing device, control system) to transmit fluid pressure readings thereto and/or allow control of the pressure transducer in any appropriate manner.

In an embodiment, any of the above medical fluid tubing sets may be usable as part of a medical fluid injection system. For instance, a medical fluid injection system may include an injection device, a multi-patient tubing section interconnected with the injection device, and any of the above-described medical fluid tubing sets. In this embodiment, the medical fluid tubing set includes or may be characterized as a patient-specific tubing section and is interconnected with the multi-patient tubing section such that the multi-patient tubing section is located between the injection device and the patient-specific tubing section. In one variation, a fluid source may be fluidly interconnected with the injection device. For instance, the fluid source may include a volume of any appropriate fluid (e.g., saline, contrast media) to accommodate multiple injections by the injection device.

A second aspect of the present invention is provided by a method of evaluating a medical fluid tubing set. The tubing set includes a first section of medical tubing and first and second check valves that are spaced along/within the first section of medical tubing. The method includes monitoring a fluid pressure in the first section of medical tubing between the first and second check valves, and assessing an operating condition of at least one of the first and second check valves based on the monitoring step.

A number of feature refinements and additional features are applicable to the second aspect of the present invention. These feature refinements and additional features may be used individually or in any combination. As such, each of the following features that will be discussed may be, but are not required to be, used with any other feature or combination of features of the second aspect. The following discussion is applicable to at least the second aspect.

In an embodiment, the monitoring step may be selected from the group consisting of mechanically monitoring the fluid pressure (e.g., with a movable element), electrically monitoring the fluid pressure (e.g., with a pressure transducer), or a combination thereof. In one variation, the method may further include a step of providing an indication upon the assessing step identifying at least a possible failure of at least one of the first and second check valves. For example, the indication may be selected from the group consisting of visual, audible, tactile, or any combination thereof.

The assessing step may be subject to a number of characterizations. In an embodiment, the assessing step may include comparing the fluid pressure from the monitoring step to a cracking pressure of at least one of the first and second check valves. In an embodiment, the assessing step may include associating a failed condition of at least one of the first and second check valves with the monitoring step identifying a predetermined drop in magnitude of the fluid pressure. In an embodiment, the assessing step may include associating a failed condition of at least one of the first and second check valves with the monitoring step identifying that the fluid pressure is less than a cracking pressure of at least one of or each of the first and second check valves. In one arrangement, the medical fluid tubing set may be discarded if the assessing step identifies an occurrence of the failed condition. In another arrangement, only a portion of the medical fluid tubing set may need to be discarded if the assessing step does not identify the occurrence of a failed condition.

In an embodiment, the method may include the steps of directing a flow of fluid through the medical fluid tubing set, opening each of the first and second check valves in response to the directing step, terminating the directing step, and closing the first and second check valves in response to the terminating step. Thereafter, the assessing step may include determining if at least one of the first and second check valves has opened after the closing step and prior to any further initiation of the directing step. For instance, it may be determined that at least one of the first and second check valves has opened if the fluid pressure identified in the monitoring step is less than a cracking pressure of at least one of the first and second check valves.

In an embodiment, a method of using a tubing arrangement may include executing any of the above-described evaluating methods. For instance, a method of using a tubing arrangement may include delivering a first fluid through the medical fluid tubing set, where the medical fluid tubing set further comprises a multi-patient section of medical tubing. The first section of medical tubing may be replaced after the first fluid delivering step, and a second fluid may be delivered through the medical fluid tubing set after the replacing step.

In one arrangement, the method may include replacing the multi-patient tubing section prior to the second fluid delivering step. Here, the replacing the multi-patient tubing section step may be executed in response to the assessing step identifying a presumed failed condition of at least one of the first and second check valves.

A number of feature refinements and additional features are separately applicable to each of above-noted first and second aspects of the present invention. These feature refinements and additional features may be used individually or in any combination in relation to each of the above-noted first and second aspects. Any feature of any other various aspects of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a power injector includes "a syringe" alone does not mean that the power injector includes only a single syringe). Moreover, any failure to use phrases such as "at least one" also does not limit the corresponding feature to the singular (e.g., indicating that a power injector includes "a syringe" alone does not mean that the power injector includes only a single syringe). Use of the phrase "at least generally" or the like in relation to a particular feature encompasses the corresponding characteristic and insubstantial variations thereof (e.g., indicating that a syringe barrel is at least generally cylindrical encompasses the syringe barrel actually being cylindrical). Finally, a reference of a feature in conjunction with the phrase "In one embodiment" does not limit the use of the feature to a single embodiment.

Any power injector that may be utilized to provide a fluid discharge may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading and/or drawing of fluid and/or so as to return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g., to discharge fluid). Each syringe plunger driver may utilize one or more drive sources of any appropriate size, shape, configuration, and/or type. Multiple drive source outputs may be combined in any appropriate manner to advance a single syringe plunger at a given time. One or more drive sources may be dedicated to a single syringe plunger driver, one or more drive sources may be associated with multiple syringe plunger drivers (e.g., incorporating a transmission of sorts to change the output from one syringe plunger to another syringe plunger), or a combination thereof. Representative drive source forms include a brushed or brushless electric motor, a hydraulic motor, a pneumatic motor, a piezoelectric motor, or a stepper motor.

Any such power injector may be used for any appropriate application where the delivery of one or more medical fluids is desired, including without limitation any appropriate medical imaging application (e.g., computed tomography or CT imaging; magnetic resonance imaging or MRI; single photon emission computed tomography or SPECT imaging; positron emission tomography or PET imaging; X-ray imaging; angiographic imaging; optical imaging; ultrasound imaging) and/or any appropriate medical diagnostic and/or therapeutic application (e.g., injection of chemotherapy, pain management, etc.). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate).

Any appropriate number of syringes may be utilized with any such power injector in any appropriate manner (e.g., detachably; front-loaded; rear-loaded; side-loaded), any appropriate medical fluid may be discharged from a given syringe of any such power injector (e.g., contrast media, therapeutic fluid, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit (e.g., medical tubing set), where this conduit is fluidly interconnected with the syringe in any appropriate manner and directs fluid to a desired location (e.g., to a catheter that is inserted into a patient for injection). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). In one embodiment, each syringe includes a syringe barrel and a plunger that is disposed within and movable relative to the syringe barrel. This plunger may interface with the power injector's syringe plunger drive assembly such that the syringe plunger drive assembly is able to advance the plunger in at least one direction, and possibly in two different, opposite directions.

As used herein, the term "fluidly interconnected" refers to two or more components or entities being connected (directly or indirectly) in a manner such that fluid can flow (e.g., unidirectionally or bidirectionally) in a predetermined flow path therebetween at least at some point in time (e.g., after opening one or more valves). For example, "an injection device fluidly interconnected to a patient" describes a configuration where fluid can flow from the injection device through any interconnecting devices (e.g., tubing, connectors) and into the patient (e.g., into the vasculature of the patient).

BRIEF DESCRIPTION OF THE FIGURES

FIG. 9 is a perspective view of another pressure sensor that may be used by the dual check valve arrangement of FIG. 5.

DETAILED DESCRIPTION

Figure 1:
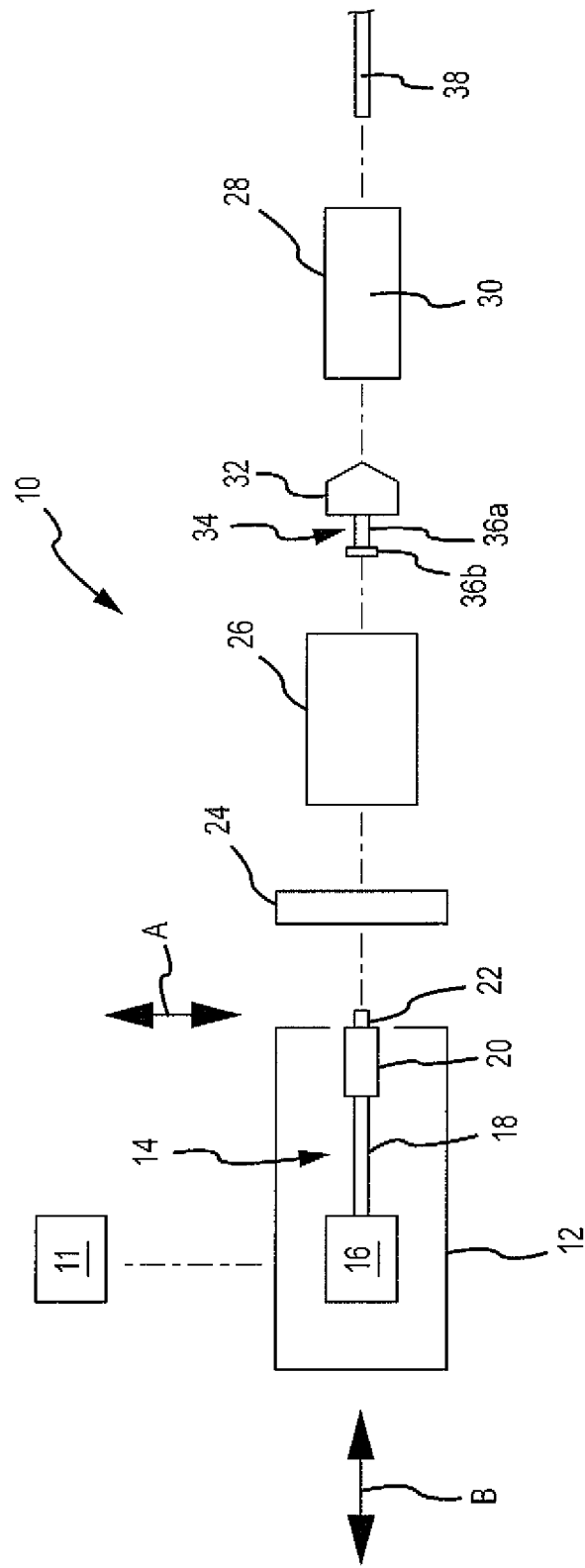
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide any of the following functions: controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on the powerhead 12 and, when installed, may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically associated with the powerhead 12 in a manner that allows the syringe 28 to be disposed therein as a part of or after installing the syringe 28 on the powerhead 12. The same pressure jacket 26 will typically remain associated with the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections and/or if the syringe(s) 28 to be utilized with the power injector 10 is (are) of sufficient durability to withstand high-pressure injections without the additional support provided by a pressure jacket 26. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 (e.g., a plunger 32 thereof) to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interacting or interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interact or interface with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 of the power injector 10 may interact with the syringe plunger 32 of the syringe 28 in any appropriate manner (e.g., by mechanical contact; by an appropriate coupling (mechanical or otherwise)) so as to be able to move or advance the syringe plunger 32 (relative to the syringe barrel 30) in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be desired. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, these components may or may not be coupled when the ram 20 advances the syringe plunger 32 to discharge fluid from the syringe 28 (e.g., the ram 20 may simply "push on" the syringe plunger coupler 34 or directly on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
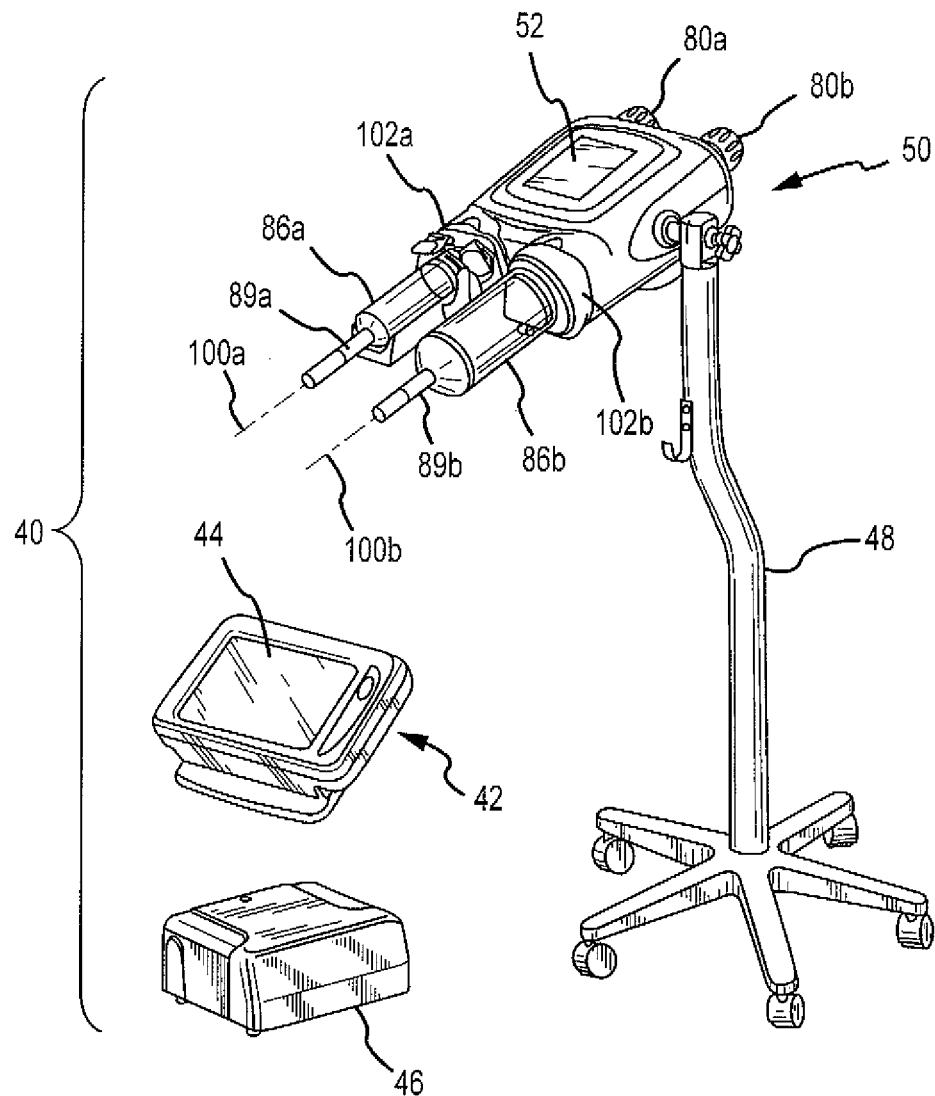
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. Two syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86a, 86b, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one or more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
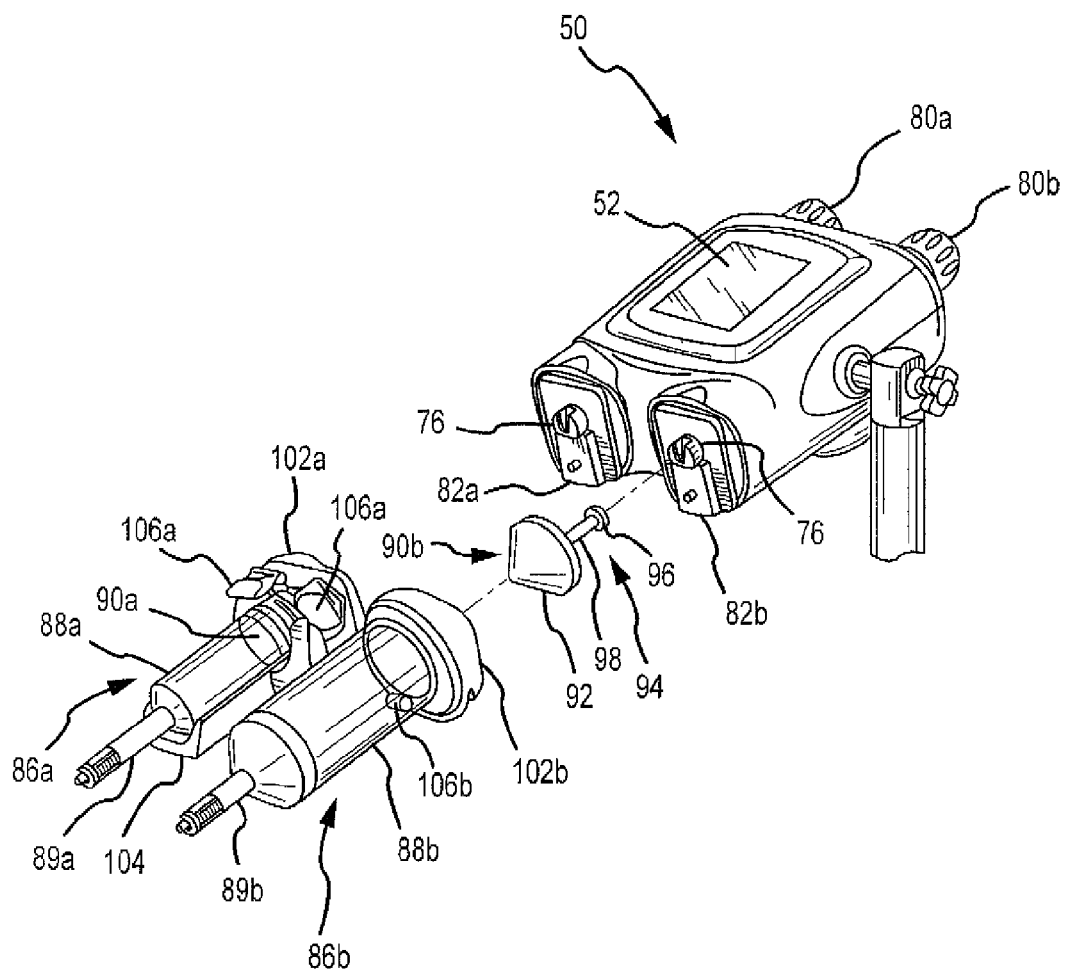
FIG. 2B is an enlarged, partially exploded, perspective view of a powerhead used by the power injector of FIG. 2A.

Various details regarding the integration of the syringes 86a, 86b with the powerhead 50 are presented in FIG. 2B. Each of the syringes 86a, 86b includes the same general components. The syringe 86a includes plunger or piston 90a that is movably disposed within a syringe barrel 88a. Movement of the plunger 90a along an axis 100a (FIG. 2A) via operation of the powerhead 50 will discharge fluid from within a syringe barrel 88a through a nozzle 89a of the syringe 86a. An appropriate conduit (not shown) will typically be fluidly interconnected with the nozzle 89a in any appropriate manner to direct fluid to a desired location (e.g., a patient). Similarly, the syringe 86b includes plunger or piston 90b that is movably disposed within a syringe barrel 88b. Movement of the plunger 90b along an axis 100b (FIG. 2A) via operation of the powerhead 50 will discharge fluid from within the syringe barrel 88b through a nozzle 89b of the syringe 86b. An appropriate conduit (not shown) will typically be fluidly interconnected with the nozzle 89b in any appropriate manner to direct fluid to a desired location (e.g., a patient).

The syringe 86a is interconnected with the powerhead 50 via an intermediate faceplate 102a. This faceplate 102a includes a cradle 104 that supports at least part of the syringe barrel 88a, and which may provide/accommodate any additional functionality or combination of functionalities. A mounting 82a is disposed on and is fixed relative to the powerhead 50 for interfacing with the faceplate 102a. A ram coupler 76 of a ram 74 (FIG. 2C), which are each part of a syringe plunger drive assembly or syringe plunger driver 56 (FIG. 2C) for the syringe 86a, is positioned in proximity to the faceplate 102a when mounted on the powerhead 50. Details regarding the syringe plunger drive assembly 56 will be discussed in more detail below in relation to FIG. 2C. Generally, the ram coupler 76 may be coupled with the syringe plunger 90a of the syringe 86a, and the ram coupler 76 and ram 74 (FIG. 2C) may then be moved relative to the powerhead 50 to move the syringe plunger 90a along the axis 100a (FIG. 2A). It may be such that the ram coupler 76 is engaged with, but not actually coupled to, the syringe plunger 90a when moving the syringe plunger 90a to discharge fluid through the nozzle 89a of the syringe 86a.

The faceplate 102a may be moved at least generally within a plane that is orthogonal to the axes 100a, 100b (associated with movement of the syringe plungers 90a, 90b, respectively, and illustrated in FIG. 2A), both to mount the faceplate 102a on and remove the faceplate 102a from its mounting 82a on the powerhead 50. The faceplate 102a may be used to couple the syringe plunger 90a with its corresponding ram coupler 76 on the powerhead 50. In this regard, the faceplate 102a includes a pair of handles 106a. Generally and with the syringe 86a being initially positioned within the faceplate 102a, the handles 106a may be moved to in turn move/translate the syringe 86a at least generally within a plane that is orthogonal to the axes 100a, 100b (associated with movement of the syringe plungers 90a, 90b, respectively, and illustrated in FIG. 2A). Moving the handles 106a to one position moves/translates the syringe 86a (relative to the faceplate 102a) in an at least generally downward direction to couple its syringe plunger 90a with its corresponding ram coupler 76. Moving the handles 106a to another position moves/translates the syringe 86a (relative to the faceplate 102a) in an at least generally upward direction to uncouple its syringe plunger 90a from its corresponding ram coupler 76.

The syringe 86b is interconnected with the powerhead 50 via an intermediate faceplate 102b. A mounting 82b is disposed on and is fixed relative to the powerhead 50 for interfacing with the faceplate 102b. A ram coupler 76 of a ram 74 (FIG. 2C), which are each part of a syringe plunger drive assembly 56 for the syringe 86b, is positioned in proximity to the faceplate 102b when mounted to the powerhead 50. Details regarding the syringe plunger drive assembly 56 again will be discussed in more detail below in relation to FIG. 2C. Generally, the ram coupler 76 may be coupled with the syringe plunger 90b of the syringe 86b, and the ram coupler 76 and ram 74 (FIG. 2C) may be moved relative to the powerhead 50 to move the syringe plunger 90b along the axis 100b (FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
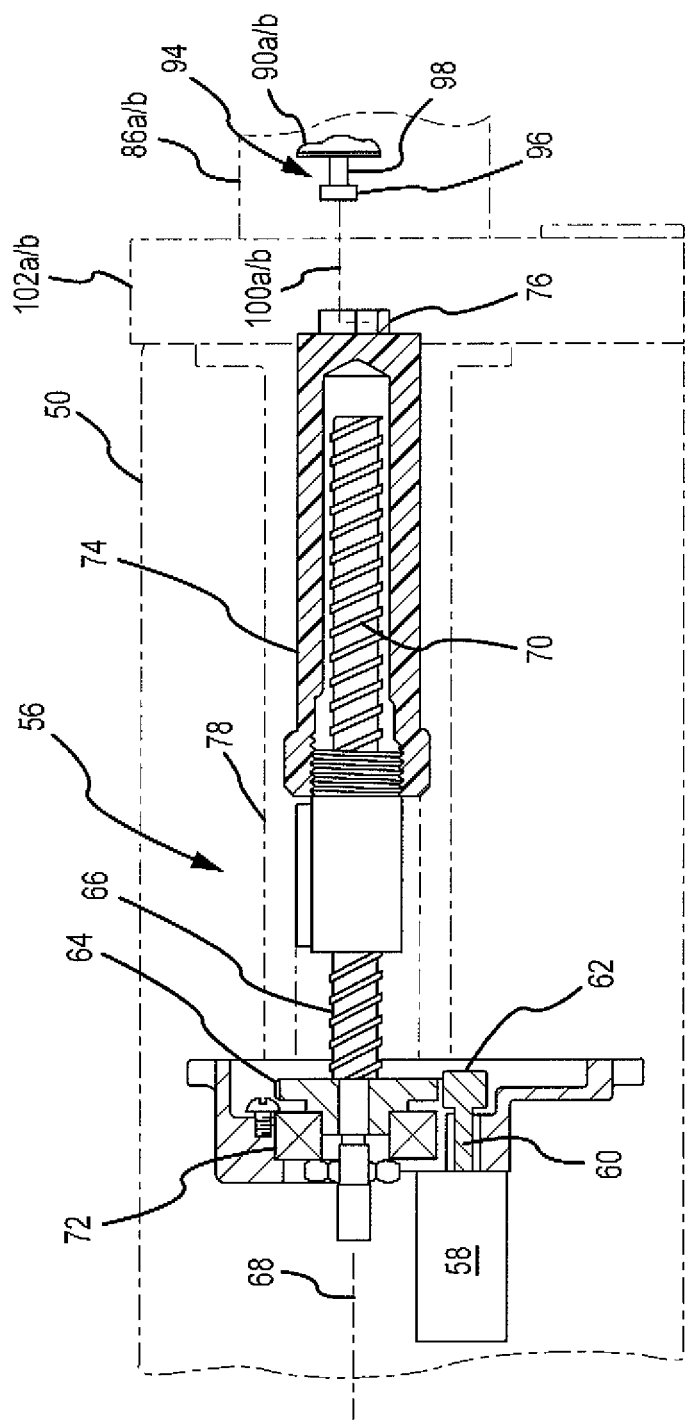
FIG. 2C is a schematic of one embodiment of a syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient) and/or any appropriate medical diagnostic and/or therapeutic application (e.g., injection of chemotherapy, pain management, etc.). Representative medical imaging applications for the power injectors 10, 40 include without limitation computed tomography or CT imaging, magnetic resonance imaging or MRI, single photon emission computed tomography or SPECT imaging, positron emission tomography or PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Multiple syringes may discharge into a common conduit (e.g., for provision to a single injection site), or one syringe may discharge into one conduit (e.g., for provision to one injection site), while another syringe may discharge into a different conduit (e.g., for provision to a different injection site). Each such syringe utilized by each of the power injectors 10, 40 may include any appropriate fluid (e.g., a medical fluid), for instance contrast media, therapeutic fluid, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
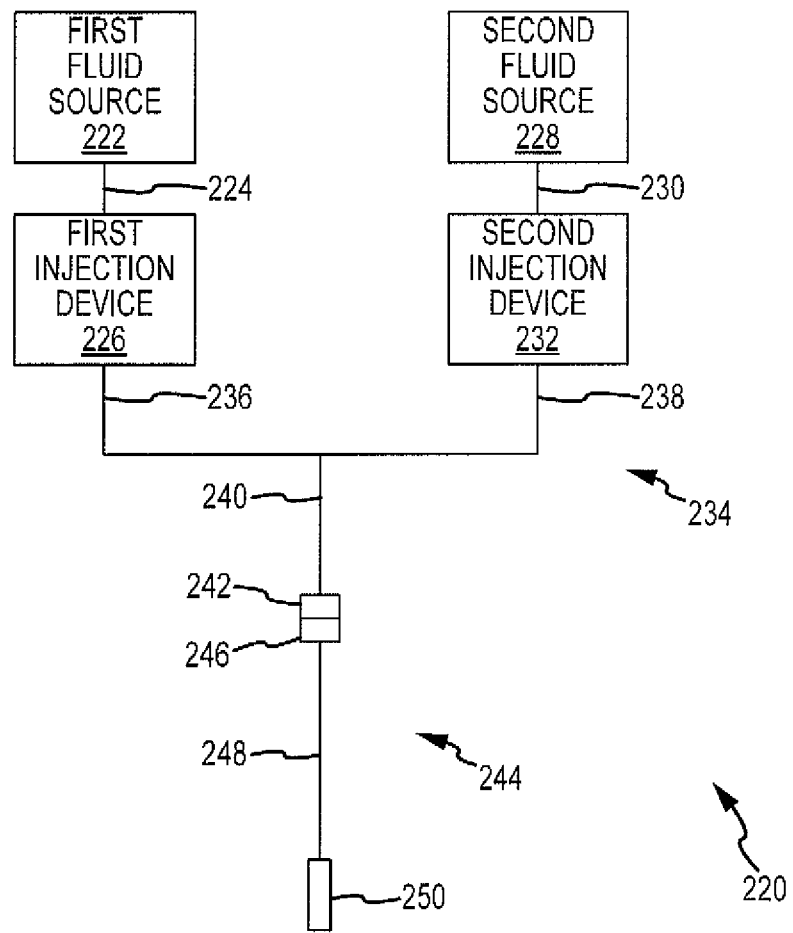
FIG. 3 is a schematic of one embodiment of a multi-dose injection system that uses both a multi-patient tubing section and a patient-specific tubing section.

FIG. 3 presents one embodiment of an injection system 220 (e.g., a multi-dose injection system; a medical fluid injection system; a multi-dose medical fluid injection system) which may incorporate one or more components of the power injector 40 of FIG. 2A. A first fluid source 222 may be fluidly interconnected with a first injection device 226 by first fluid source tubing 224. A second fluid source 228 may be fluidly interconnected with a second injection device 232 by second fluid source tubing 230. Any appropriate fluid may be utilized by each of the first fluid source 222 and the second fluid source 228. In one embodiment, the first fluid source 222 utilizes contrast media, while the second fluid source 228 utilizes saline or any other appropriate biocompatible flushing media. Each of the first fluid source 222 and the second fluid source 228 may have a fluid volume that is sufficient for multiple injections or injection procedures (e.g., for multiple patients).

The first injection device 226 and the second injection device 232 each may be of any appropriate size, shape, configuration, and/or type (e.g., a power injector). The first fluid source tubing 224 and the second fluid source tubing 230 each may be in the form of any appropriate conduit (e.g., medical tubing). Any appropriate component or combination of components may be incorporated in either one or each of the first fluid source tubing 224 and the second fluid source tubing 230 (e.g., one or more valves of any appropriate type).

A reusable, multi-use or multi-patient section of tubing 234 may be fluidly interconnected with each of the injection devices 226, 232. There may be three different parts or sections of the multi-patient tubing section 234—first injection device tubing 236 that extends from the first injection device 226, second injection device tubing 238 that extends from the second injection device 232, and common discharge tubing 240. Fluid discharged from the first injection device 226 may be directed into the first injection device tubing 236, and then into the common discharge tubing 240. Fluid discharged from the second injection device 232 may be directed into the second injection device tubing 238, and then into the common discharge tubing 240.

The first injection device tubing 236, the second injection device tubing 238, and the common discharge tubing 240 may be integrally formed, or one or more appropriate connectors may be utilized to fluidly interconnect adjacent sections of the multi-patient tubing section 234. An appropriate connector may be used to install the first injection device tubing 236 to the first injection device 226, while an appropriate connector may be used to install the second injection device tubing 238 to the second injection device 232. A connector 242 of any appropriate type may be provided at a free end of the common discharge tubing 240.

A disposable, single-use, single-patient, or patient-specific tubing set or tubing section 244 may be fluidly interconnected with the common discharge tubing 240 of the multi-patient tubing section 234 by a connector 246 of any appropriate type such that the multi-patient tubing section 234 is located between the first and second injection devices 226, 232 and the patient-specific tubing section 244. The patient-specific tubing section 244 includes tubing 248. An appropriate vasculature access device (e.g., a catheter) 250 may be appropriately interconnected with the tubing 248 (e.g., via an appropriate connector).

Any appropriate component or combination of components may be incorporated in either one or each of the multi-patient tubing section 234 and the patient-specific tubing section 244 (e.g., one or more valves of any appropriate type). The tubing utilized by each of the multi-patient tubing section 234 and the patient-specific tubing section 244 may be of any appropriate type (e.g., medical tubing).

Figure 4:
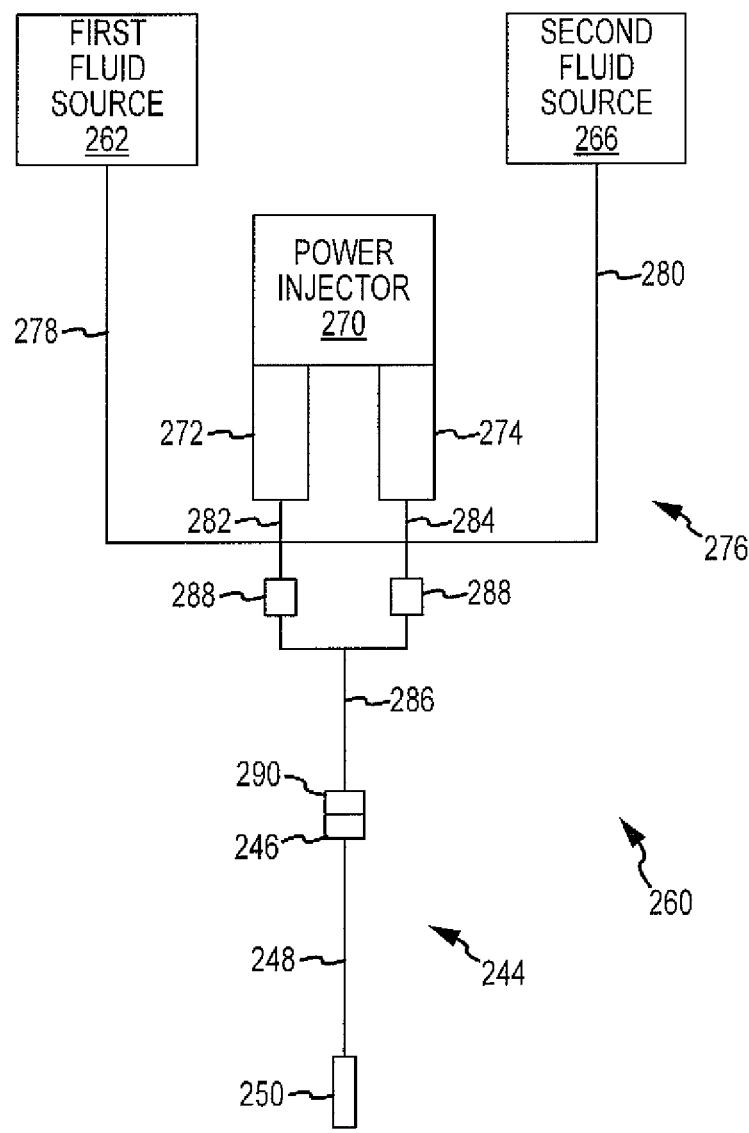
FIG. 4 is a schematic of another embodiment of a multi-dose injection system that uses both a multi-patient tubing section and a patient-specific tubing section.

FIG. 4 presents another embodiment of an injection system 260 (e.g., a multi-dose injection system; a medical fluid injection system; a multi-dose medical fluid injection system). The injection system 260 may include a first fluid source 262, a second fluid source 266, a power injector 270, a reusable or multi-patient section of tubing 276, and the above-discussed patient-specific tubing section 244. The first fluid source 262 may be fluidly interconnected with a first syringe 272 installed on the power injector 270 by first fluid source tubing 278 (which may be part of the multi-patient tubing section 276). The second fluid source 266 may be fluidly interconnected with a second syringe 274 installed on the power injector 270 by second fluid source tubing 280 (which may be part of the multi-patient tubing section 276). Any appropriate fluid may be utilized by each of the first fluid source 262 and the second fluid source 266. In one embodiment, the first fluid source 262 utilizes contrast media, while the second fluid source 266 utilizes saline or any other appropriate biocompatible flushing media. Each of the first fluid source 262 and the second fluid source 266 may have a fluid volume that is sufficient for multiple injections or injection procedures (e.g., for multiple patients). The first fluid source tubing 278 and the second fluid source tubing 280 each may be in the form of any appropriate conduit (e.g., medical tubing). Any appropriate component or combination of components may be incorporated in either one or each of the first fluid source tubing 278 and the second fluid source tubing 280 (e.g., one or more valves of any appropriate type).

The multi-patient tubing section 276 may include first syringe tubing 282 that extends from the first syringe 272 on the power injector 270, second syringe tubing 284 that extends from the second syringe 274 on the power injector 270, and common discharge tubing 286. Fluid discharged by the power injector 270 from the first syringe 272 is directed into the first syringe tubing 282, and then into the common discharge tubing 286. Fluid discharged by the power injector 270 from the second syringe 274 is directed into the second syringe tubing 284, and then into the common discharge tubing 286.

The first fluid source tubing 278, the second fluid source tubing 280, the first syringe tubing 282, the second syringe tubing 284, and the common discharge tubing 286 may be integrally formed, an appropriate connector may be utilized to fluidly interconnect each pair of adjacent sections of the multi-patient tubing section 276, or part of the multi-patient tubing section 276 may be integrally formed with one or more other portions of the multi-patient tubing section 276 being incorporated by one or more connectors. An appropriate connector may be used to install the first syringe tubing 282 to the first syringe 272, while an appropriate connector may be used to install the second syringe tubing 284 to the second syringe 274. A connector 290 of any appropriate type may be provided at a free end of the common discharge tubing 286.

Any appropriate component or combination of components may be incorporated in either one or each of the multi-patient tubing section 276 and the patient-specific tubing section 244 as previously noted (e.g., one or more valves of any appropriate type). For instance, each of the first syringe tubing 282 and the second syringe tubing 284 may include an appropriate valve 288 (e.g., a stopcock) to allow fluid from the fluid sources 262, 266 to be loaded into the respective syringes 272, 274 without being directed into the patient-specific tubing section 244. The tubing utilized by the multi-patient tubing section 276 may be of any appropriate type (e.g., medical tubing).

Figure 5:
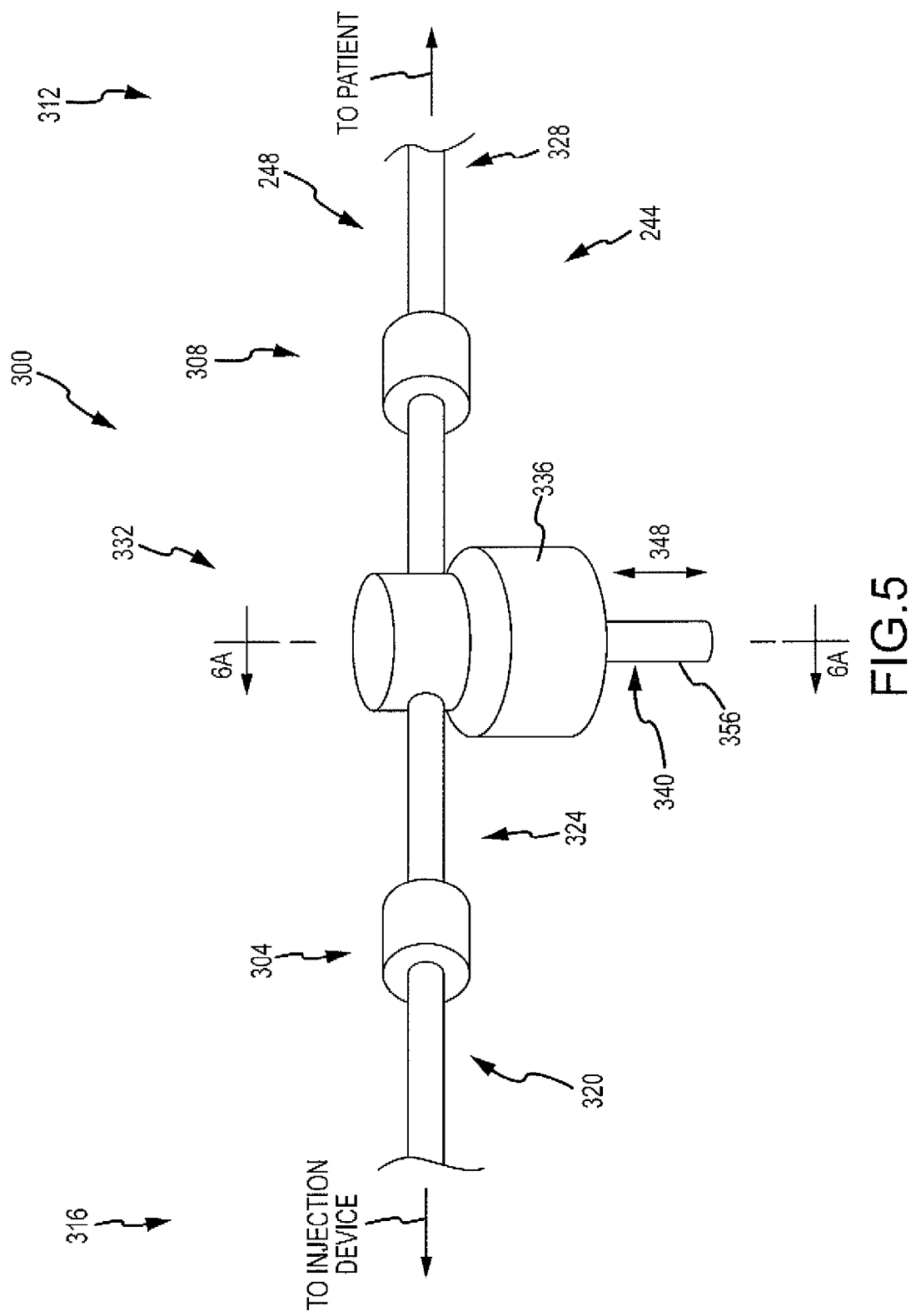
FIG. 5 is a perspective view of one embodiment of a dual check valve arrangement that may be used by the patient-specific tubing sections from the multi-dose injection systems of FIGS. 3 and 4.

FIG. 5 presents a dual check valve arrangement 300 that may be used by the injection systems 220, 260 of FIGS. 3 and 4, or any other appropriate fluid delivery system. For instance, the arrangement 300 may be incorporated into the patient-specific tubing section 244 of FIGS. 3 and 4, although it is contemplated that the arrangement 300 could be appropriately incorporated into any other portion of tubing (e.g., medical tubing) where it is desired to at least attempt to reduce the potential for fluid flow from one side of the arrangement 300 (e.g., downstream side 312) to another side of the arrangement 300 (e.g., upstream side 316). Hereafter, the check valve arrangement 300 may be described in relation to the injection system 220 of FIG. 3 and where the arrangement 300 is incorporated into the patient-specific tubing section 244 (although the discussion is of course equally applicable to the injection system 260 of FIG. 4). As such: 1) the upstream side 316 of the arrangement 300 would be located between the multi-patient tubing section 234 and the downstream side 312 of the arrangement 300; and 2) the downstream side 312 of the arrangement 300 would be located between the vasculature access device 250 and the upstream side 316 of the arrangement 300.

The arrangement 300 broadly includes first and second check valves 304, 308, respectively (which hereafter may be simply referred to collectively as "first and second check valves 304, 308"), appropriately disposed along/within tubing 248 that includes first, second and third portions 320, 324, 328, respectively. The first and second check valves 304, 308, along with the tubing 248, each may be of any appropriate size, shape, configuration and/or type. The arrangement 300 also includes what may be characterized as a sterility detection device in the form of a pressure sensor 332 that will be more fully described below. It will be appreciated that the arrangement 300 may serve to at least attempt to reduce the potential for fluid flow from the patient-specific tubing section 244 upstream (e.g., in a direction "To Injection Device" as indicated in FIG. 5) into the multi-patient tubing section 234 (illustrated in FIG. 3; or into the multi-patient tubing section 276 in the injection system 260 of FIG. 4) and thus at least attempt to only allow fluid flow downstream (e.g., in a direction "To Patient" as indicated in FIG. 5). In this regard, the arrangement 300 may at least attempt to reduce the potential for contamination of the multi-patient tubing section 234 with fluids from any patient. As such, the multi-patient tubing section 234 may be used to supply fluid to one or more patients by the arrangement 300. The first and second check valves 304, 308 may each be in the form of a one-way check valve (i.e., configured to allow flow in only a single direction, when functioning properly) and may be appropriately serially disposed along/within the tubing 248 (e.g., the check valves 304, 308 are disposed in spaced relation within the flow path through the tubing 248). Such an arrangement provides a level of redundancy in that if one of the one-way check valves fails, the other one-way check valve may remain functional and reduce the potential of backflow of fluids from the patient into the multi-patient tubing section 234.

The pressure sensor 332 broadly serves to provide at least one user-perceptible indication (e.g., visual, tactile, audible, or any combination thereof) that one or both (e.g., at least one) of the first and second check valves 304, 308 may have failed. Stated otherwise, the pressure sensor 332 may provide at least one signal to a user that the sterile barrier between the downstream and upstream sides 312, 316, respectively, of the arrangement 300 may be properly functioning (e.g., is in tact) and/or may have failed. The pressure sensor 332 functions at least in part by appropriately monitoring for a failed condition of at least one of the first and second check valves 304, 308 (e.g., that at least one of the first and second check valves is at least presumed to have failed, and thereby including a situation where only one of the check valves 304, 308 may have failed, or where both of the check valves 304, 308 may have failed) by appropriately measuring, recording or otherwise monitoring (e.g., mechanically and/or electrically) a first region of fluid pressure in the second portion 324 of tubing 248 in the portion of the flow path extending between the first and second check valves 304, 308.

Each of the first and second check valves 304, 308 may require a fluid pressure differential between upstream and downstream sides of each of the first and second check valves 304, 308 (hereinafter "fluid pressure differential") that is equal to or greater than a "cracking pressure" (i.e., the minimum amount by which the upstream pressure of a check valve must be greater than the downstream pressure of the check value before the first and second check valves 304, 308 will open and allow fluid to flow in the downstream direction). Thereafter, when the fluid pressure differential of each of the first and second check valves 304, 308 drops below its respective cracking pressure, each of the first and second check valves 304, 308 should close assuming normal operation, and thus attempt to prevent fluid from flowing from its downstream side to its upstream side. At this point (assuming each of the first and second check valves 304, 308 has the same cracking pressure), the fluid pressure within the second portion 324 of tubing 248 should always be equal to or greater than the cracking pressure of at least one of the check valves 304, 308.

For instance, assume each of the first and second check valves 304, 308 has a cracking pressure of 0.5 psi, fluid is flowing through the tubing 248 and the first and second check valves 304, 308 at 10 psi in the downstream direction (e.g., to a patient), and that the fluid pressure differential of each check valve 304, 308 is greater than its cracking pressure (e.g., each of the first and second check valves 304, 308 is open). After the fluid source is turned off or the flow is otherwise stopped, the upstream pressure of each of the first and second check valves 304, 308 will drop such that the fluid pressure differential falls to a level approximately equal to the cracking pressure and the first and second check valves 304, 308 should close. When both of the first and second check valves 304, 308 close, the fluid pressure within the second portion 324 of the tubing 248 should remain constant (as no fluid should be able to pass through the properly functioning first and second check valves 304, 308 in the upstream direction) and in this example may be approximately equal to just less than 10 psi. Nevertheless, what is important is that the fluid pressure will always be at least about equal to or above the cracking pressure of the first and second check valves 304, 308 assuming normal functioning of the first and second check valves 304, 308. Thus, assuming the fluid pressure within the second portion 324 of tubing 248 is equal to or above the cracking pressure of the first and second check valves 304, 308, only the patient-specific tubing section 244 (that incorporates the arrangement 300) and/or other downstream components needs to be replaced before a subsequent injection using the injection system 220 (e.g., in relation to a different patient).

When the fluid pressure within the second portion 324 of the tubing 248 drops below the cracking pressure of the first and second check valves 304, 308, however, it may be assumed that at least one of the first and second check valves 304, 308 has allowed fluid to flow from its downstream side to its upstream side and that the sterile barrier between the downstream and upstream sides 312, 316, respectively, of the arrangement 300 may have failed. As such, it may be necessary at this point to replace all components of the injection system 220 that have been in contact with the fluid (e.g., both the patient-specific tubing section 244 and the multi-patient tubing section 234 (which again has incorporated the arrangement 300)).

Figure 6A:
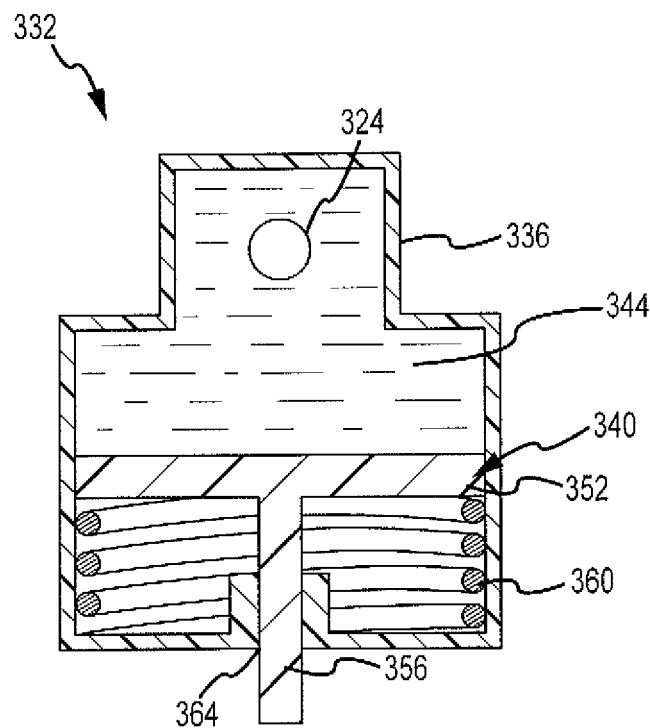
FIG. 6A is a cross-sectional view of a pressure sensor that may be used by the dual check valve arrangement of FIG. 5, taken along the line 6-6 in FIG. 5, illustrating a condition in which both of the check valves are presumed to be operative.
Figure 6B:
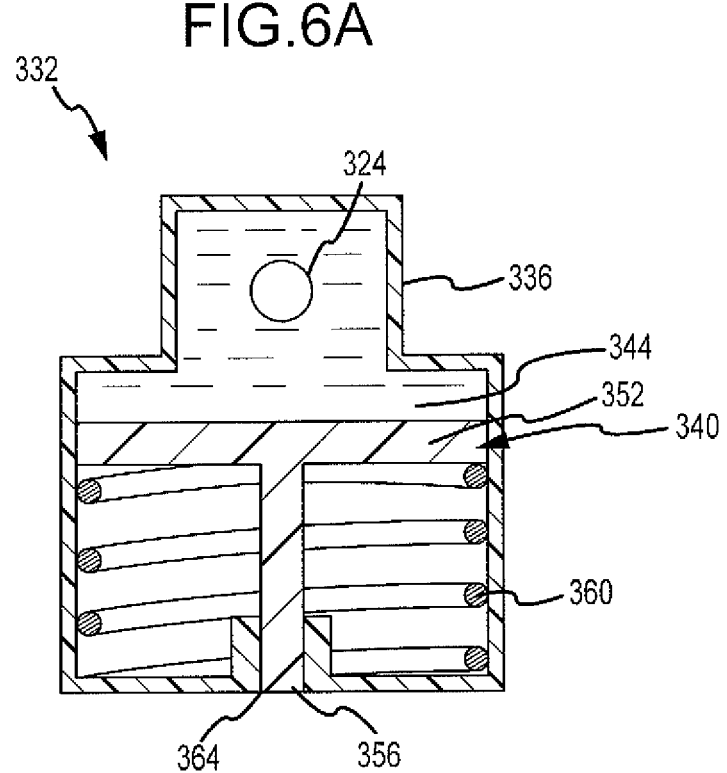
FIG. 6B is a cross-sectional view of the pressure sensor from FIG. 6A, illustrating a condition in which at least one of the check valves is at least presumed to have failed.

With reference now to FIGS. 5, 6A, and 6B, one embodiment of the pressure sensor 332 for monitoring for a failed condition of at least one of the first and second check valves 304, 308 is illustrated. The pressure sensor 332 is operable to appropriately monitor (e.g., measure, record, observe) the fluid pressure within the second portion 324 of tubing 248 and provide a user-perceptible indication that one or more of the first and second check valves 304, 308 may have failed. The pressure sensor 332 may be fluidly interconnectable with the tubing 248 and may be situated in series in the flow path between the first and second check valves 304, 308 on the second portion 324 of tubing 248. The pressure sensor 332 may include a housing 336, a movable element 340 that is movable relative to the housing 336, and a biasing member in the form of a spring 360, each of which may be of any appropriate size, shape, configuration and/or type. Generally, the position of the movable element 340 relative to the housing 336 is at least influenced by the magnitude of the fluid pressure within the pressure sensor 332, or more specifically the pressure within the second portion 324 of tubing 248.

The second portion 324 of tubing 248 may be appropriately fluidly interconnected to the housing 336, allowing fluid within the injection system 200 to pass into and out of a chamber 344 (illustrated in FIGS. 6A and 6B) within the housing 336. In this regard, it may be assumed that the fluid pressure within the second portion 324 of tubing 248 is at least approximately equal to the fluid pressure within the chamber 344. A portion (e.g., movable element 340) of the pressure sensor 332 may be operable to change from a first state to a second state (e.g., from the position in FIG. 6B to the position in FIG. 6A) upon the fluid pressure within the second portion 324 becoming equal to or above a predetermined fluid pressure level (e.g., the cracking pressure of the first and second check valves 304, 308). Furthermore, the movable element 340 may be operable to change from the second state back to the first state (e.g., from the position in FIG. 6A to the position in FIG. 6B) upon the fluid pressure within the second portion 324 of tubing 248 (corresponding to the pressure within the chamber 344) falling below the predetermined fluid pressure level. For instance, the movable element 340 may be operable to move along an axial direction 348 between the first and second states.

Now referring in particular to FIGS. 6A and 6B, the movable element 340 may include a piston 352 (e.g., a substantially non-deformable piston) and a piston rod 356. While the piston 352 and piston rod 356 are shown as being integrally connected, it will be appreciated that the piston 352 and piston rod 356 may be appropriately bonded or otherwise connected to each other. The piston 352 may be operable to slide or otherwise move within the chamber 344 in a first direction (e.g., away from the second portion 324 of tubing 248) in response to fluid pressure within the second portion 324 of tubing 248 and chamber 344, and in a second direction (e.g., towards the second portion 324 of tubing 248; opposite of the noted first direction) in response to a biasing force from a biasing member which may be in the form of a spring 360 (e.g., coil, compression) that may be appropriately interconnected (e.g., permanently, removably) to and/or interact with the movable element 340 and one or more portions of the housing 336. Any appropriate biasing member or combination of biasing members may be utilized to bias the movable element 340 toward the noted second position.

The piston 352 of the movable element 340 may be designed to reduce the potential of fluid flow between a first side of the piston 352 (e.g., adjacent to the chamber 344; the side that interfaces with the chamber 344) and an opposite second side of the piston 352. The piston rod 356 may extend from the opposite second side of the piston 352 and be operable to appropriately selectively slide and protrude through an opening 364 in the housing 336 in a manner as described below. What is of importance with regard to the movable element 340 is as follows: 1) the position of the movable element 340 relative to the housing 336 is influenced by the pressure within the chamber 344, which is directly related to the pressure within the second portion 324 of tubing 248; and 2) when there is a change in pressure within the chamber 344 that is indicative of a failure of one or both of the check valves 304, 308, the position of the movable element 340 relative to the housing 336 should change, and this change in position should be visually discernible exteriorly of the pressure sensor 332 (e.g., by a resulting change in shape of the pressure sensor 332).

The spring 360 may be selected (e.g., according to spring constant, kind and grade of material, number of coils, controlling diameter) to provide a biasing force against a portion of the movable element 340 (e.g., piston 352) that is just less than the predetermined fluid pressure level (e.g., the cracking pressure of the first and second check valves 304, 308). In this regard, until fluid in the patient-specific tubing section 244 has been pressurized to at least the cracking pressure of the first and second check valves 304, 308, the biasing force created by the spring 360 should serve to urge the movable element 340 in the second direction towards the second portion 324 of tubing 248 where the piston rod 356 may be at least substantially concealed by the housing 336 (more generally, a retracted position) as illustrated in FIG. 6B. Thereafter, once fluid in the patient-specific tubing section 244 has been pressurized to at least the cracking pressure of the first and second check valves 304, 308, such fluid pressure should overcome the biasing force created by the spring 360 and urge the movable element 340 in the first direction away from the second portion 324 of the tubing 248 until the piston rod 356 protrudes from the housing 336 as illustrated in FIG. 6A (more generally, a protruded position or a more protruded position than that described above). At this point and assuming normal functionality of the first and second check valves 304, 308, the piston rod 356 should remain protruded from the housing 336 because the fluid pressure within the second portion 324 of the tubing 248 (and hence the chamber 344) should not drop below the predetermined fluid pressure level (e.g., the cracking pressure of the first and second check valves 304, 308) as previously described if the check valves 304, 308 are functioning properly. In this regard, a protruded or first orientation or position of the movable element 340 as illustrated in FIG. 6A may be associated with a proper functioning of the first and second check valves 304, 308. The piston rod 356 may be appropriately marked or indicated (e.g., brightly colored or patterned) to aid a user in perceiving the protruded first orientation of the piston rod 356. As previously discussed, only the patient-specific tubing section 244 (incorporating the tubing arrangement 300) may need to be replaced after an injection procedure if the movable element 340 has remained in the protruded first orientation or position.

In the case of fluid pressure within the second portion 324 of the tubing 248 and chamber 344 falling below the predetermined fluid pressure level, the spring 360 should overcome such fluid pressure and urge the movable element 340 in the second direction towards the second portion 324 of the tubing 248. The biasing force generated by the spring 360 should move the piston rod 356 to a retracted position (e.g., into the housing 336) where it may become at least substantially concealed by the housing 336 as illustrated in FIG. 6B. As a drop in fluid pressure within the second portion 324 and chamber 344 below the predetermined fluid pressure level may signal that at least one of the first and second check valves 304, 308 has at least presumably failed, a substantially concealed or second orientation or position of the movable element 340 may be associated with a failed condition of at least one of the first and second check valves 304, 308 and indicate that now both the patient-specific and multi-patient tubing sections 244, 234, respectively, should be replaced before a subsequent injection procedure.

The pressure sensor 332 may be characterized as changing shape or appearance to provide a visual indication of at least a potential failure of the check valve 304, the check valve 308, or both. The pressure sensor 332 is of one shape at a time when both of the check valves 304, 308 are at least presumed to be functional (FIG. 6A, and where the piston rod 356 is an extended or protruded position). The pressure sensor 332 is of a different shape at a time when at least one of the check valves 304, 308 may have failed (FIG. 6B, and where the piston rod 356 is less extended compared to the FIG. 6A position (generally, a retracted position), and where the piston rod 356 may in fact be concealed by the housing 336).

While the cracking pressure of the first check valve 304 has been discussed as being the same as that of the second check valve 308, in other embodiments the first and second check valves 304, 308 may have different cracking pressures. In this regard, the predetermined fluid pressure level may be intentionally created to be different than the cracking pressure of the first and second check valves 304, 308. For instance, the first check valve 304 may be chosen to have a cracking pressure less than that of the second check valve 308. As the second check valve 308 would thus require a greater pressure differential than does the first check valve 304 to open, it may be more sensitive to pressure fluctuations in the patient-specific tubing section 244. Thus, upon a decrease in fluid pressure within the patient-specific tubing section 244, the second check valve 308 may close before the first check valve 304, and thus the fluid within the second portion 324 and chamber 344 may maintain a pressure that is less than the cracking pressure of the second check valve 308 even when both of the first and second check valves 304, 308 are properly functioning. Thus, the predetermined fluid pressure level for the arrangement 300 in this situation may be designed to be at a pressure that is between the cracking pressure of the first and second check valves 304, 308. Accordingly, the spring 360 may be designed to provide a biasing force against the movable element 340 that is just less than such a predetermined fluid pressure level. Other arrangements of first and second check valves 304, 308 having various cracking pressures accordingly creating various predetermined fluid pressure levels are also envisioned.

Figure 7A:
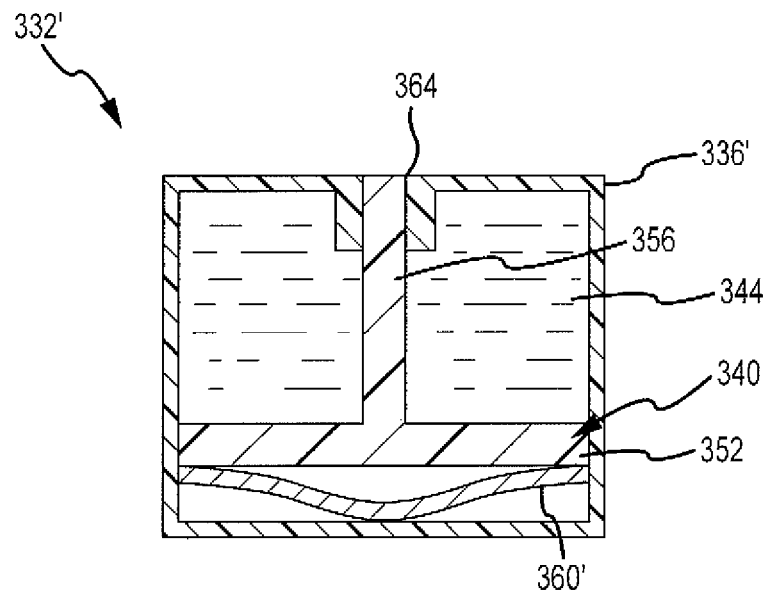
FIG. 7A is a cross-sectional view of another pressure sensor that may be used by the dual check valve arrangement of FIG. 5, illustrating a condition in which both of the check valves are presumed to be operative.
Figure 7B:
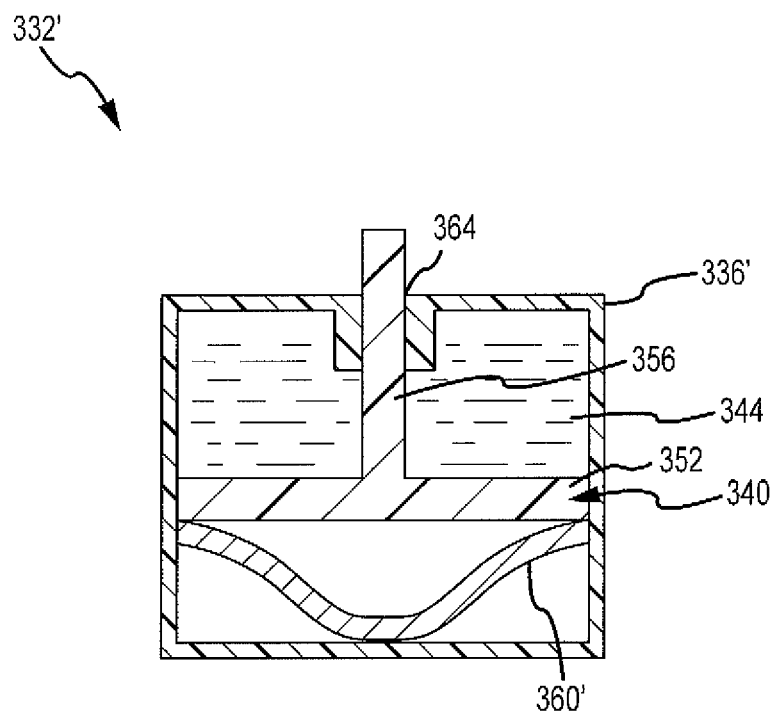
FIG. 7B is a cross-sectional view of the pressure sensor from FIG. 7A, illustrating a condition in which at least one of the check valves is at least presumed to have failed.

FIGS. 7A and 7B present another embodiment of a pressure sensor that may be used in place of the pressure sensor 332 of FIGS. 5, 6A and 6B. Corresponding components between the embodiments are identified by common reference numerals. Those corresponding components that differ in at least some respect from the embodiment of FIGS. 5, 6A and 6B are identified by a "single prime" designation in FIGS. 7A and 7B. The one or more components of the pressure sensor 332' may be of any appropriate size, shape, configuration and/or type. For instance, the pressure sensor 332' may include a housing 336' having a moveable element 340 and a spring 360' (or any other appropriate biasing member or combination of biasing members) appropriately mounted within the housing 336' to indicate that at least one of the first and second check valves 304, 308 is at least presumed to have failed. The primary differences between the pressure sensor 332 of FIGS. 5, 6A and 6B and the pressure sensor 332' of FIGS. 7A and 7B are: the use of a wave spring as the spring 360' in place of the compression spring of FIGS. 5 and 6 (although other types of springs (e.g., compression) and/or biasing members could also be used); and a substantially concealed or first position or orientation of the movable element 340 as illustrated in FIG. 7A to indicate a normal or proper function of the first and second check valves 304, 308 and a protruded or second position or orientation as illustrated in FIG. 7B to indicate at least a presumed failure or failed condition of at least one of the first and second check valves 304, 308, instead of vice versa as in FIGS. 5, 6A and 6B. That is and for the case of the pressure sensor 332', the movable element 340 is in a retracted position when the check valves 304, 308 are at least presumed to be functional, and moves to an extended or more protruded position when at least one of the check valves 304, 308 is at least presumed to have failed.

In the embodiment of FIGS. 7A and 7B, the spring 360' may be appropriately selected to provide a biasing force against the movable element 340 (e.g., against the piston 352) that urges the movable element 340 into the second position (such that the piston rod 356 protrudes from the housing 336', as shown in FIG. 7B) upon the fluid pressure within the second portion 324 of tubing 248 and the chamber 344 dropping below the predetermined fluid pressure level. Again, the piston rod 356 may be appropriately patterned or colored such that when a user observes the piston rod 356, a failed condition of at least one of the first and second check valves 304, 308 may be presumed, thereby indicating that the patient-specific and multi-patient sections 244, 234 should both be replaced before a subsequent injection procedure (e.g., for a second patient). It should be appreciated that the piston rod 356 could be incorporated by the spring 360' (alleviating the need for the piston 352—the spring 360' therefore being in the form of a diaphragm or the like that is exposed to the fluid in the chamber 344).

Figure 8A:
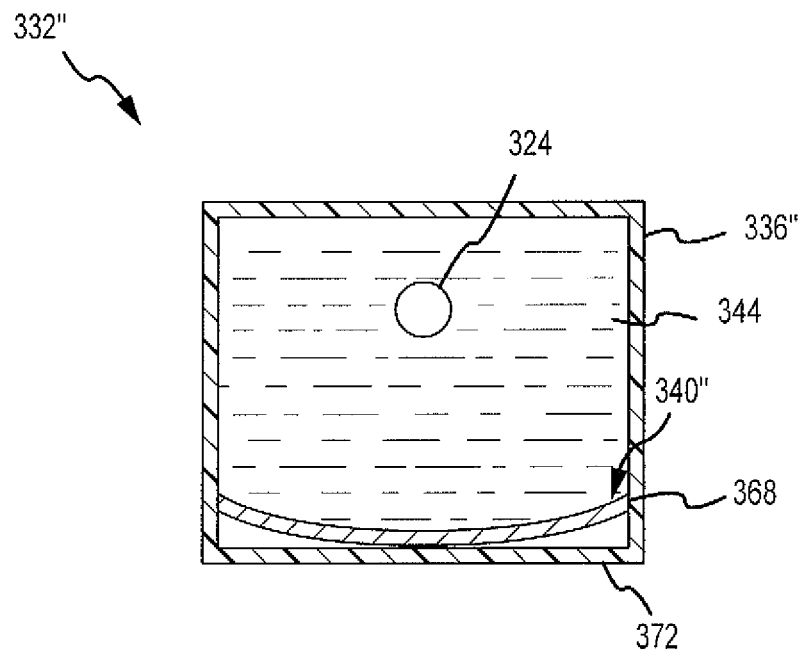
FIG. 8A is a cross-sectional view of another pressure sensor that may be used by the dual check valve arrangement of FIG. 5, illustrating a condition in which both of the check valves are presumed to be operative.
Figure 8B:
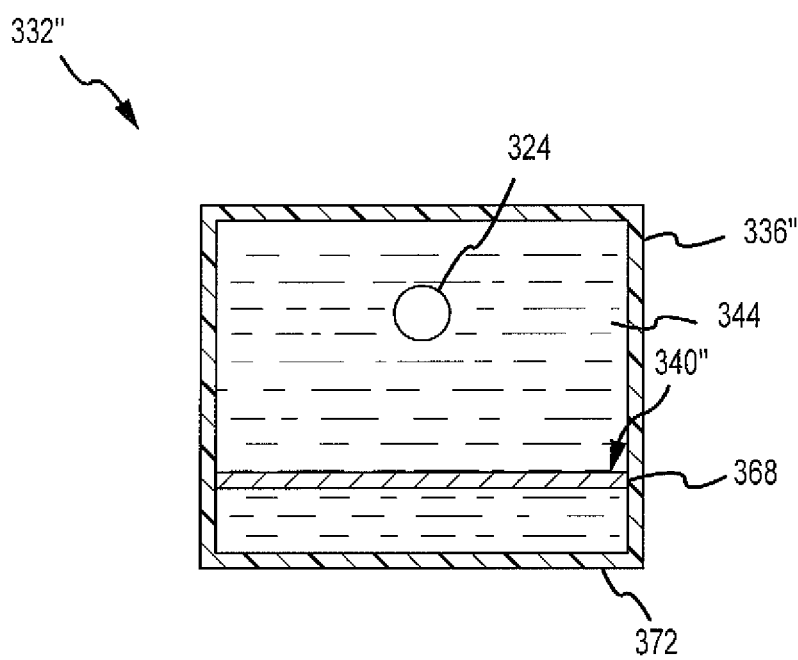
FIG. 8B is a cross-sectional view of the pressure sensor from FIG. 8A, illustrating a condition in which at least one of the check valves is at least presumed to have failed.

FIGS. 8A and 8B present another embodiment of the pressure sensor 332 of FIGS. 5, 6A, and 6B, and corresponding components between the embodiments are identified by common reference numerals. Those corresponding components that differ in at least some respect from the embodiment of FIGS. 5, 6A, and 6B are identified by a "double prime" designation in FIGS. 8A and 8B. The one or more components of the pressure sensor 332" may be of any appropriate size, shape, configuration and/or type. The primary difference between the pressure sensor 332 of FIGS. 5, 6A, and 6B and the pressure sensor 332" of FIGS. 8A and 8B is the use of a flexible diaphragm 368 as the movable element 340" instead of the spring 360, piston 352 and piston rod 356 of FIGS. 5, 6A and 6B, as well as the use of a window 372 (e.g., transparent; semi-transparent) that allows for external viewing for some type of change in relation to the diaphragm 368 (e.g., a change in state of some type). One state of the diaphragm 368 is associated with presumed proper functioning of the check valves 304, 308, and the other state of the diaphragm 368 is associated with an at least presumed failure of either one or both of the check valves 304, 308. The pressure sensor 332" may be configured such that the diaphragm 368 is visible through the window 372 when the check valves 304, 308 are presumed to be functioning properly and not visible through the window 372 when at least one of the check valves 304, 308 is at least presumed to have failed, or vice versa.

In the embodiment of FIGS. 8A and 8B, the flexible diaphragm 368 may be appropriately selected to provide a biasing force that urges the flexible diaphragm 368 into a position such that it is not discernable (e.g., visually) from an exterior of the pressure sensor 332" through the window 372. Thus, when a user can visually observe or otherwise discern the existence or presence of the flexible diaphragm 368 through the window 372 (e.g., a first position or orientation, shown in FIG. 8A), the fluid pressure within the second portion 324 of tubing 248 and chamber 344 is presumably equal to or above the predetermined fluid pressure level, and the first and second check valves 304, 308 are presumed to be in a normal or proper functioning condition. When the user can no longer visually observe or otherwise discern the existence of presence of the flexible diaphragm 368 through the window 372 (e.g., a second position or orientation, shown in FIG. 8B), fluid pressure within the second portion 324 of tubing 248 and the chamber 344 has dropped below the predetermined fluid pressure level and a failed condition of at least one of the first and second check valves 304, 308 may be presumed.

The housing 336" may include any appropriate portion that aids in attempting to visually discern the existence or presence of the flexible diaphragm 368 upon the fluid pressure within the second portion 324 of tubing 248 assuming a pressure equal to or above the predetermined fluid pressure level. For instance, the housing 336" may include the noted window 372 (e.g., a transparent or semi-transparent portion) through which the flexible diaphragm 368 may be discernable in the first position and which is not discernable in the second position in one embodiment. For instance, the flexible diaphragm 368 may actually come into contact with the window 372 when the flexible diaphragm 368 is in its first position in the illustrated embodiment (associated with a condition where the check valves 304, 308 are at least presumed to be functioning properly) and may not contact the window 372 when the flexible diaphragm 368 is in its second position in the illustrated embodiment (associated with a condition where at least one of the check valves 304, 308 is presumed to have failed).

An exterior of the flexible diaphragm 368 could also undergo a visually-discernable shape change when transitioning between the first and second positions, where the flexible diaphragm 368 would be visible through the window 372 in each of the first and second positions. In any case, the flexible diaphragm 368 may be appropriately patterned or colored to aid a user in visually perceiving or otherwise discerning the flexible diaphragm 368 in at least its first position (again, associated with a presumed normal working condition of the first and second check valves 304, 308). Other portions of the housing 336" may also be at least semi-transparent to aid in visually perceiving the flexible diaphragm 368. While pressure sensors including either a biasing element (e.g., spring) and movable element and/or a flexible diaphragm have been discussed, it is contemplated that any other mechanical device that responds to fluid pressure may be appropriately utilized in conjunction with or as part of the pressure sensor for measuring or otherwise monitoring the fluid pressure within the patient-specific tubing section 244 between the first and second check valves 304, 308.

FIG. 9 presents another embodiment of the pressure sensor 332 of FIGS. 5, 6A, and 6B. Corresponding components between the embodiments are identified by common reference numerals. Those corresponding components that differ in at least some respect from the embodiment of FIGS. 5, 6A and 6B are identified by a "triple prime" designation in FIG. 9. The one or more components of the pressure sensor 332''' may be of any appropriate size, shape, configuration and/or type. The primary differences between the pressure sensor 332 of FIGS. 5, 6A, and 6B and the pressure sensor 332''' of FIG. 9 are: the use of a housing 336''' that includes a fluid port 376 instead of the movable element 340 and spring 360; and a reusable pressure transducer 380 of any appropriate type (e.g., piezoresistive, capacitive) interconnected to the fluid port 376 for measuring or otherwise monitoring fluid pressure within the second portion 324 and chamber 344 (not shown in FIG. 9). More generally, whereas the above-described embodiments are based upon mechanical movements that is visually discernible to provide an indication that at least one of the check valves 304, 308 may have failed, the embodiment of FIG. 9 may be characterized as acquiring a pressure measurement and sending a resulting signal (e.g., electrical, optical) that may be used to provide an indication of at least a potential failure of one or both of the check valves 304, 308.

As the fluid port 376 provides access to the chamber 344 of the housing 336''', the port 376 may be characterized as being fluidly interconnectable with the second portion 324 of the tubing 248. Furthermore, the fluid port 376 of the housing 336''' and a portion of the pressure transducer 380 may have corresponding mating structures (not labeled) to allow the pressure transducer 380 to be removably fluidly interconnected to the chamber 344 of the housing 336'''. As an example, an inside surface of the fluid port 376 and a portion of the pressure transducer 380 could be correspondingly threaded or have any other appropriate types of mating structures. In one arrangement, the pressure transducer 380 may be a self-contained arrangement that is operable to provide a user-perceptible or discernable signal (e.g., visual, audible, tactile) or feedback that the fluid pressure within the chamber 344 and second portion 324 is at least one of below, equal to or above the predetermined fluid pressure level or that the multi and patient-specific tubing section 234, 244 are undergoing an initial pressurization to purge air from the injection system 220 (e.g., at the beginning of an injection procedure). For instance, the pressure transducer 380 may include a first colored light (e.g., LED, not shown) that indicates that the multi and patient-specific tubing section 234, 244 are undergoing an initial pressurization and have not yet reached the predetermined fluid pressure level, a different second colored light that indicates a normal working condition of the first and second check valves 304, 308 (e.g., the fluid pressure within the chamber 344 is equal to or above the predetermined fluid pressure level), and a different third colored light that indicates a failed condition of at least one of the first and second check valves 304, 308 (e.g., the fluid pressure within the chamber 344 is below predetermined fluid pressure level). As another example, the pressure transducer 380 may include one or more audible signals to indicate at least one of an initial pressurization, a normal condition and a failed condition.

In other arrangements, the pressure transducer 380 may be in appropriate communication (e.g., via signal line 384, wirelessly) with any type of computing device or control system that would allow a user to control the pressure transducer 384 and/or obtain fluid pressure readings therefrom. In one arrangement, the pressure transducer 384 may be appropriately coupled to another component of the injection system 220 (e.g., console 42 and/or GUI 52 of FIG. 2A) so that the injection system 220 can, inter alia, appropriately notify (e.g., audible, visual) a user of a working or failed condition of the first and second check valves 304, 308, display a message to change the multi-patient and/or patient-specific tubing sections 234, 244, and/or attempt to prevent reuse of the multi-patient and/or patient-specific tubing sections 234, 244. It will be appreciated that after a procedure on a first patient, the pressure transducer 380 may be appropriately removed or disconnected (e.g., unscrewed) from the housing 336''' and then reattached or connected to the housing 3366''' of another (e.g., a new) patient-specific tubing section 244 for a subsequent procedure (e.g., on another patient). To allow such reuse of the pressure transducer 380, the pressure transducer 380 may be isolated by an appropriate diaphragm. The pressure transducer 380 may also be appropriately sterilized between uses.

Figure 10:
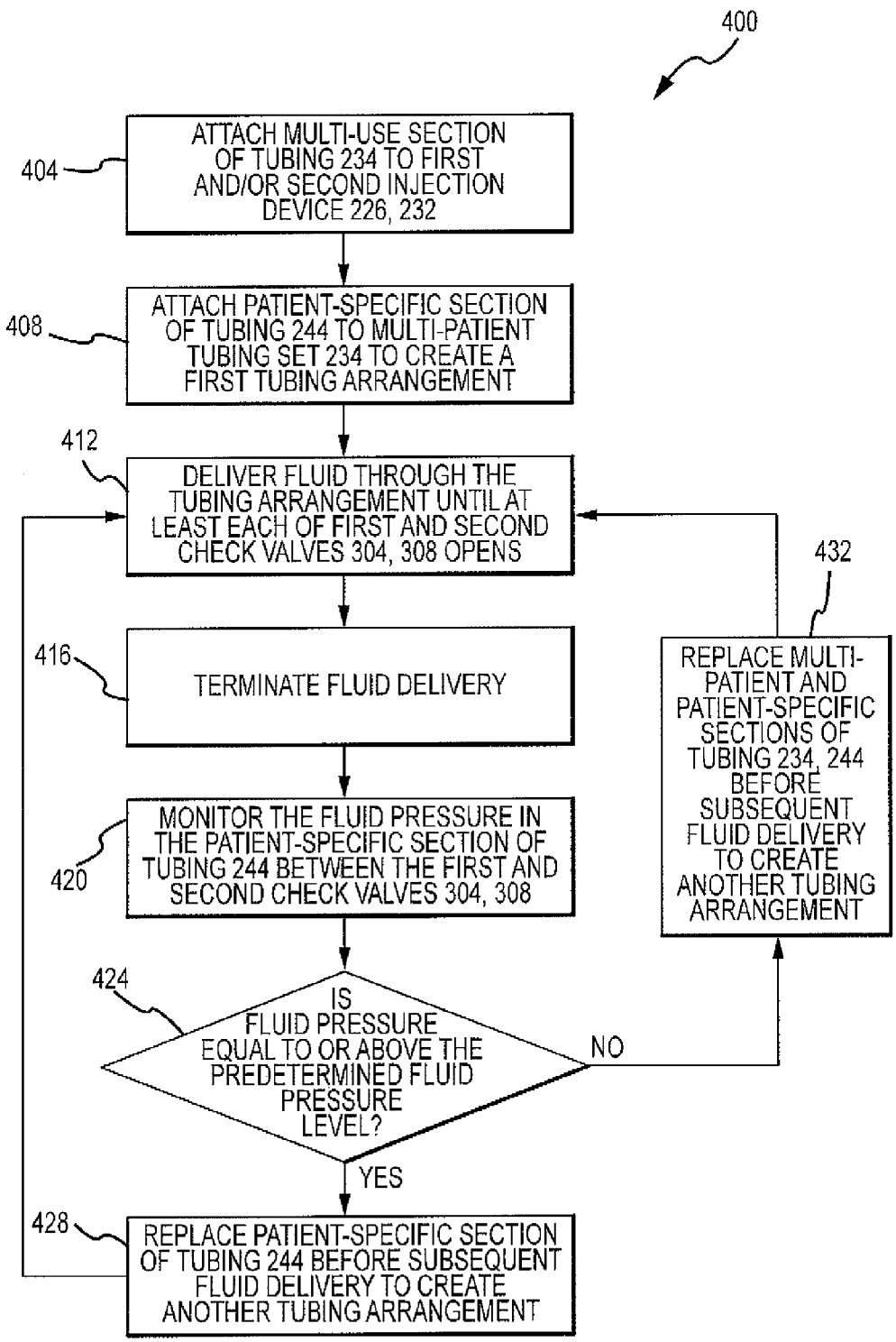
FIG. 10 is a flowchart of a method of using and/or evaluating a tubing arrangement (e.g., medical fluid tubing set).

FIG. 10 is a flowchart of a method 400 of using and/or evaluating a tubing arrangement (e.g., medical fluid tubing set). One step 404 may be to appropriately fluidly interconnect or otherwise attach a new multi-use tubing section 234 to the first and/or second injection device 226, 232. Any appropriate connectors may be used to install the multi-use tubing section 234 to the first and/or second injection device 226, 232. In step 408, a patient-specific tubing section 244 may be fluidly interconnected or otherwise attached with the multi-patient tubing section 234 by a connector of any appropriate type such that the multi-patient tubing section 234 is located between the first and second injection devices 226, 232 and the patient-specific tubing section 244. At this point, the multi-patient and patient-specific tubing sections 234, 244 function as a first tubing arrangement or tubing set. Also as part of this step, any appropriate vasculature access device (e.g., a catheter) may be appropriately interconnected with the patient-specific tubing section 244 via an appropriate connector, although the vasculature access device may also be interconnected to the patient-specific tubing section 244 before the patient-specific tubing section 244 is interconnected with the multi-patient tubing section 234.

The next step 412 may be to deliver or otherwise direct a flow of fluid through the tubing arrangement until at least each of the first and second check valves 304, 308 opens (e.g., until the fluid pressure in the patient-specific tubing section 244 becomes equal to or higher than the cracking pressure of the first and second check valves 304, 308). This step 412 may serve the function of purging air from the injection system and readying the injection system for an injection sequence. At some later point in time, fluid delivery may be terminated in step 416 after which each of the first and second check valves 304, 308 should eventually close assuming normal working conditions of the first and second check valves 304, 308. Pursuant to step 420, fluid pressure in the patient-specific tubing section 244 between the first and second check valves 304, 308 may be appropriately monitored. This pressure-monitoring function of step 420 may be executed after step 412 and/or after step 416. It will be appreciated that the monitoring of step 420 may be selected from the group consisting of electrically monitoring the fluid pressure, mechanically monitoring the fluid pressure, or a combination of electrically and mechanically monitoring the fluid pressure (e.g., using any of the embodiments described herein).

One form of monitoring the fluid pressure may be measuring the fluid pressure (e.g., absolute) within the patient-specific tubing section 244 between the first and second check valves 304, 308. An operating condition of one of the first and second check valves 304, 308 may be assessed based on the monitoring performed in step 420. For instance, one manner of assessing the operating condition may be to determine whether the monitored fluid pressure is equal to or above the predetermined fluid pressure level in step 424. As previously discussed, the predetermined fluid pressure level may be equal to the cracking pressure of the first and second check valves 304, 308 or may be equal to a fluid pressure above or below the cracking pressure of at least one of the first and second check valves 304, 308 if the first and second check valves 304, 308 are selected to have different cracking pressures. Nevertheless, if the monitored fluid pressure is equal to or above the predetermined fluid pressure level, the patient-specific tubing section 244 may be discarded and replaced in step 428 before subsequent fluid delivery. The original multi-patient and new patient-specific tubing sections 234, 244 now form another (e.g., second) tubing arrangement and the method may return to step 412 to again deliver fluid through the tubing arrangement (e.g., for another patient) until at least each of the first and second check valves 304, 308 opens.

If the monitored fluid pressure is not equal to or above (e.g., is less than) the predetermined fluid pressure through the execution of step 420, a failed condition of at least one of the first and second check valves 304, 308 may be presumed. Stated otherwise, it may be presumed that at least one of the first and second check valves 304, 308 has opened or otherwise not closed properly and has let fluid flow upstream towards the multi-patient tubing section 234. As this scenario may have resulted in the contamination of the multi-patient tubing section 234 with fluid from the patient-specific tubing section 244, it may be required to discard and replace both the multi-patient and patient-specific tubing sections 234, 244 before a subsequent fluid delivery operation is initiated. Other actions may also be required (e.g., replacement of one or more syringes on the associated injection device). The new multi-patient and patient-specific tubing sections 234, 244 now form another tubing arrangement or tubing set, and the method may return to step 412 to again deliver fluid through the tubing arrangement (e.g., for another patient) until at least each of the first and second check valves 304, 308 opens. In other arrangements, a failed condition of at least one of the first and second check valves 304, 308 may be presumed if the monitoring from step 420 identifies a predetermined drop in magnitude. Nonetheless, a presumed failed condition of at least one of the first and second check valves 304, 308 may result in a user-perceptible indication being provided that is selected from the group consisting of visual, audible, tactile, or any combination of visual, audible or tactile.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A medical fluid tubing set, comprising:
   a multi-patient tubing section that is reusable for injection of multiple patients;
   a patient-specific tubing section downstream of and detachably connected to said multi-patient tubing section, wherein said patient-specific tubing section is located between said multi-patient tubing section and a patient when delivering fluid to the patient, and wherein said patient-specific tubing section comprises:
   first and second check valves that are spaced along said patient-specific tubing section;
   a pressure sensor fluidly connected with a first region of said patient-specific tubing section that extends between said first and second check valves, wherein said pressure sensor is responsive to a fluid pressure in said first region of said patient-specific tubing section and comprises means for monitoring for a failed condition, wherein said failed condition is a presumption that at least one of said first and second check valves has failed by remaining open when said at least one of said first and second check valves should be closed, wherein said pressure sensor comprises a movable element that undergoes a change in position when said fluid pressure within said first region falls below a predetermined fluid pressure level to identify said failed condition, wherein said predetermined fluid pressure level is a cracking pressure of at least one of said first and second check valves and where a check valve cracking pressure is a minimum amount by which an upstream pressure of the check valve must be greater than a downstream pressure of the check valve before the check valve will open when functioning properly, wherein said change in position of said movable element is visually perceptible from an exterior of said pressure sensor, wherein a first position of said movable element is associated with a presumed proper functioning of said first and second check valves, and wherein a second position of said movable element is associated with said failed condition; and
   a biasing member that is interconnected with said movable element, wherein said biasing member biases said movable element toward said second position, and wherein a biasing force applied to said movable element is less than said predetermined fluid pressure level.

2. The medical fluid tubing set of claim 1, wherein said predetermined fluid pressure level is said cracking pressure of each of said first and second check valves.

3. The medical fluid tubing set of claim 1, wherein said pressure sensor is situated on said patient-specific tubing section.

4. The medical fluid tubing set of claim 1, wherein said first check valve, said pressure sensor, and said second check valve are situated in series along said patient-specific tubing section.

5. The medical fluid tubing set of claim 1, wherein said pressure sensor is situated between said first and second check valves.

6. The medical fluid tubing set of claim 1, wherein said pressure sensor further comprises a housing.

7. The medical fluid tubing set of claim 6, wherein said movable element comprises a portion that protrudes from said housing in said first position and is substantially concealed by said housing in said second position.

8. The medical fluid tubing set of claim 6, wherein said movable element comprises a portion that protrudes from said housing in said second position and is substantially concealed by said housing in said first position.

9. The medical fluid tubing set of claim 6, wherein at least a portion of said movable element is discernable in one of said first and second positions and is generally not discernable in the other of said first and second positions.

10. The medical fluid tubing set of claim 9, wherein said housing comprises a window, wherein said at least a portion of said movable element is discernable through said window in one of said first and second positions and is not discernable through the window in the other of said first and second positions.

11. The medical fluid tubing set of claim 1, wherein said biasing member is selected from the group consisting of a compression spring, a wave spring, or any combination thereof.

12. The medical fluid tubing set of claim 1, wherein said movable element comprises a piston that interfaces with a fluid within said first region between said first and second check valves, and wherein said piston is at least substantially non-deformable.

13. The medical fluid tubing set of any of claim 1, wherein said pressure sensor further comprises a housing, wherein said housing comprises a window, wherein said movable element comprises a diaphragm, wherein said diaphragm is visible through said window in each of said first and second positions, and wherein said diaphragm experiences a visually-discernable shape change in response to an at least presumed failed condition of at least one of said first and second check valves in changing from said first position to said second position.

14. A medical fluid tubing set, comprising:
a multi-patient tubing section that is reusable for injection of multiple patients;
a patient-specific tubing section downstream of and detachably connected to said multi-patient tubing section, wherein said patient-specific tubing section is located between said multi-patient tubing section and a patient when delivering fluid to the patient, and wherein said patient-specific tubing section comprises:
first and second check valves that are spaced along said patient-specific tubing section;
a pressure sensor fluidly connected with a first region of said patient-specific tubing section that is between said first and second check valves, wherein said pressure sensor is responsive to a fluid pressure in said first region of said patient-specific tubing section and comprises:
a housing;
a movable element incorporated by said housing;
a biasing member;
a first configuration where a fluid pressure in said first region is greater than a predetermined fluid pressure level and that disposes said movable element in a first position relative to said housing, wherein said predetermined fluid pressure level is a cracking pressure of at least one of said first and second check valves and where a check valve cracking pressure is a minimum amount by which an upstream pressure of the check valve must be greater than a downstream pressure of the check valve before the check valve will open when functioning properly; and
a second configuration where said fluid pressure in said first region is less than said predetermined fluid pressure level and said movable element is disposed in a second position relative to said housing by said biasing member, wherein said fluid pressure in said first region is less than said predetermined fluid pressure level when at least one of said first and second check valves has failed due to said at least one of said first and second check valves being open when at least one of said first and second check valves should be closed;
wherein said biasing member exerts a biasing force on said movable member that directs said movable element toward said second position, and wherein said biasing force is less than said predetermined fluid pressure level;
wherein at least part of said movable element is visible from an exterior of said pressure sensor in at least one of said first and second positions of said movable element relative to said housing; and
wherein a change of said movable element from said first position to said second position is visually perceptible from said exterior of said pressure sensor.

15. The medical fluid tubing set of claim 14, wherein said predetermined fluid pressure level is a cracking pressure of each of said first and second check valves.

16. The medical fluid tubing set of claim 14, wherein said pressure sensor is situated on said patient-specific tubing section.

17. The medical fluid tubing set of claim 14, wherein said first check valve, said pressure sensor, and said second check valve are situated in series along said patient-specific tubing section.

18. The medical fluid tubing set of claim 14, wherein said pressure sensor is situated between said first and second check valves.

19. The medical fluid tubing set of claim 14, wherein said movable element comprises a portion that protrudes from said housing in said first position and is substantially concealed by said housing in said second position.

20. The medical fluid tubing set of claim 14, wherein said movable element comprises a portion that protrudes from said housing in said second position and is substantially concealed by said housing in said first position.

21. The medical fluid tubing set of claim 14, wherein at least a portion of said movable element is discernable in one of said first and second positions and is generally not discernable in the other of said first and second positions.

22. The medical fluid tubing set of claim 21, wherein said housing comprises a window, wherein said at least a portion of said movable element is discernable through said window in one of said first and second positions and is not discernable through the window in the other of said first and second positions.

23. The medical fluid tubing set of claim 14, wherein said biasing member is selected from the group consisting of a compression spring, a wave spring, or any combination thereof.

24. The medical fluid tubing set of claim 14, wherein said movable element comprises a piston that interfaces with a fluid within said first region between said first and second check valves, and wherein said piston is at least substantially non-deformable.

25. The medical fluid tubing set of any of claim 14, wherein said housing comprises a window, wherein said movable element comprises a diaphragm, wherein said diaphragm is visible through said window in each of said first and second positions, and wherein said diaphragm experiences a visually-discernable shape change in response to an at least presumed failed condition of at least one of said first and second check valves in changing from said first position to said second position.

* * * * *